(12) United States Patent
Fahey

(10) Patent No.: US 10,987,510 B2
(45) Date of Patent: *Apr. 27, 2021

(54) SYSTEMS AND METHODS FOR AUTOMATED MUSCLE STIMULATION

(71) Applicant: SAGE PRODUCTS, LLC, Cary, IL (US)

(72) Inventor: Brian J. Fahey, Redwood City, CA (US)

(73) Assignee: Sage Products, LLC, Cary, IL (US)

(*) Notice: Subject to any disclaimer, the term of this patent is extended or adjusted under 35 U.S.C. 154(b) by 17 days.

This patent is subject to a terminal disclaimer.

(21) Appl. No.: 16/417,524

(22) Filed: May 20, 2019

(65) Prior Publication Data
US 2019/0269903 A1    Sep. 5, 2019

Related U.S. Application Data

(60) Continuation of application No. 15/091,494, filed on Apr. 5, 2016, now Pat. No. 10,293,152, which is a
(Continued)

(51) Int. Cl.
*A61N 1/04* (2006.01)
*A61N 1/36* (2006.01)
(Continued)

(52) U.S. Cl.
CPC .......... *A61N 1/0492* (2013.01); *A61B 5/0492* (2013.01); *A61B 5/4523* (2013.01);
(Continued)

(58) Field of Classification Search
USPC ............................................. 607/48–50, 148
See application file for complete search history.

(56) References Cited

U.S. PATENT DOCUMENTS 4,108,146 A   8/1978  Golden
4,390,023 A   6/1983  Rise
(Continued)

FOREIGN PATENT DOCUMENTS

FR    2596654 A    10/1987
JP    2001-025510 A    1/2001
(Continued)

OTHER PUBLICATIONS

Baker et al.; Effects of waveform on comfort during neuromuscular electrical stimulation; Clin Ortho Res; vol. 233; pp. 75-85; Aug. 1988.
(Continued)

*Primary Examiner* — Nicole F Lavert
*Assistant Examiner* — Nicole F Johnson
(74) *Attorney, Agent, or Firm* — Foley & Lardner LLP

(57) ABSTRACT

A method of electrically stimulating a target muscle of a patient includes placing at least one stimulation electrode in electrical contact with the target muscle and applying an electrical signal to the stimulation electrode. The method further includes obtaining a signal from a sensing element placed on the patient, wherein the sensing element is configured to detect at least one biological parameter of the patient associated with contraction of the target muscle caused by the application of the electrical signal, and adapting stimulation of the target muscle by the at least one stimulation electrode using the obtained signal.

20 Claims, 15 Drawing Sheets

Related U.S. Application Data continuation of application No. 14/532,595, filed on Nov. 4, 2014, now Pat. No. 9,302,104, which is a division of application No. 13/647,249, filed on Oct. 8, 2012, now Pat. No. 8,892,210, which is a continuation-in-part of application No. 12/497,230, filed on Jul. 2, 2009, now Pat. No. 8,285,381.

(60) Provisional application No. 61/133,777, filed on Jul. 2, 2008, provisional application No. 61/189,558, filed on Aug. 19, 2008, provisional application No. 61/190,602, filed on Aug. 29, 2008, provisional application No. 61/201,877, filed on Dec. 15, 2008, provisional application No. 61/544,113, filed on Oct. 6, 2011.

(51) Int. Cl.
*A61B 5/0492* (2006.01)
*A61H 39/00* (2006.01)
*A61B 5/00* (2006.01)
*A61B 90/00* (2016.01)

(52) U.S. Cl.
CPC .......... *A61B 5/4836* (2013.01); *A61B 5/6828* (2013.01); *A61B 5/6841* (2013.01); *A61B 90/39* (2016.02); *A61H 39/002* (2013.01); *A61N 1/0452* (2013.01); *A61N 1/0476* (2013.01); *A61N 1/3603* (2017.08); *A61N 1/36003* (2013.01); *A61B 5/4585* (2013.01); *A61B 2090/3904* (2016.02); *A61H 2201/165* (2013.01); *A61H 2201/5005* (2013.01); *A61H 2201/5015* (2013.01); *A61H 2201/5061* (2013.01); *A61H 2201/5084* (2013.01); *A61H 2201/5092* (2013.01); *A61H 2201/5097* (2013.01); *A61H 2205/10* (2013.01); *A61H 2205/104* (2013.01); *A61H 2230/045* (2013.01); *A61H 2230/655* (2013.01)

(56) References Cited

U.S. PATENT DOCUMENTS

| | | | |
|---|---|---|---|
| 4,480,830 A | 11/1984 | Petrofsky et al. |
| 4,580,569 A | 4/1986 | Petrofsky |
| 4,619,266 A | 10/1986 | Hodgson |
| 4,736,752 A | 4/1988 | Munck et al. |
| 4,805,636 A | 2/1989 | Barry et al. |
| 4,811,742 A | 3/1989 | Hassel et al. |
| 4,838,272 A | 6/1989 | Lieber |
| 4,962,761 A | 10/1990 | Golden |
| 4,969,468 A | 11/1990 | Byers et al. |
| 5,010,896 A | 4/1991 | Westbrook |
| 5,016,635 A | 5/1991 | Graupe |
| 5,070,873 A | 12/1991 | Graupe |
| 5,097,828 A | 3/1992 | Deutsch |
| 5,314,423 A | 5/1994 | Seney |
| 5,336,255 A | 8/1994 | Kanare et al. |
| 5,397,338 A | 3/1995 | Grey et al. |
| 5,507,788 A | 4/1996 | Lieber |
| 5,549,656 A | 8/1996 | Reiss |
| 5,674,262 A | 10/1997 | Tumey |
| 5,702,323 A | 12/1997 | Poulton |
| 5,702,429 A | 12/1997 | King |
| 5,843,152 A | 12/1998 | Tu et al. |
| 5,871,526 A | 2/1999 | Gibbs et al. |
| 5,902,328 A | 5/1999 | LaFontaine et al. |
| 6,173,198 B1 | 1/2001 | Schulze et al. |
| 6,216,704 B1 | 4/2001 | Ingle et al. |
| 6,266,558 B1 | 7/2001 | Gozani et al. |
| 6,301,500 B1 | 10/2001 | Van Herk et al. |
| 6,324,432 B1 | 11/2001 | Rigaux et al. |
| 6,341,237 B1 | 1/2002 | Hurtado |
| 6,350,276 B1 | 2/2002 | Knowlton |
| 6,480,731 B1 | 11/2002 | DeLuca et al. |
| 6,505,078 B1 | 1/2003 | King et al. |
| 6,567,696 B2 | 5/2003 | Voznesensky et al. |
| 6,829,510 B2 | 12/2004 | Nathan et al. |
| 6,840,955 B2 | 1/2005 | Ein |
| 6,944,503 B2 | 9/2005 | Crowe et al. |
| 7,146,220 B2 | 12/2006 | Dar et al. |
| 7,172,564 B2 | 2/2007 | Bosco |
| 7,204,832 B2 | 4/2007 | Altshuler et al. |
| 7,221,980 B2 | 5/2007 | Kotlik et al. |
| 7,236,832 B2 | 6/2007 | Hemmerling et al. |
| 7,257,448 B2 | 8/2007 | Crowe et al. |
| 7,473,251 B2 | 1/2009 | Knowlton et al. |
| 7,483,738 B2 | 1/2009 | Tamarkin et al. |
| 7,499,746 B2 | 3/2009 | Buhlmann et al. |
| 8,019,402 B1 | 9/2011 | Kryzpow et al. |
| 8,216,218 B2 | 7/2012 | Burns et al. |
| 8,285,381 B2 | 10/2012 | Fahey |
| 8,433,403 B2 | 4/2013 | Fahey |
| 8,588,901 B2 | 11/2013 | Fahey |
| 8,676,332 B2 | 3/2014 | Fahey |
| 8,892,210 B2 | 11/2014 | Fahey |
| 9,126,039 B2 | 9/2015 | Fahey |
| 9,149,386 B2 | 10/2015 | Fahey et al. |
| 9,302,104 B2 | 4/2016 | Fahey |
| 2002/0049483 A1 | 4/2002 | Knowlton |
| 2002/0095080 A1 | 7/2002 | Cory et al. |
| 2002/0143365 A1 | 10/2002 | Herbst |
| 2002/0151951 A1 | 10/2002 | Axelgaard et al. |
| 2002/0161415 A1 | 10/2002 | Cohen et al. |
| 2003/0114892 A1 | 6/2003 | Nathan et al. |
| 2003/0229385 A1 | 12/2003 | Elkins |
| 2004/0044384 A1 | 3/2004 | Leber et al. |
| 2004/0173220 A1 | 9/2004 | Harry et al. |
| 2004/0254624 A1 | 12/2004 | Johnson |
| 2005/0288730 A1 | 12/2005 | Deem et al. |
| 2006/0030906 A1 | 2/2006 | Carroll |
| 2006/0142816 A1 | 6/2006 | Fruitman et al. |
| 2007/0106343 A1 | 5/2007 | Monogue et al. |
| 2007/0178579 A1 | 8/2007 | Ross et al. |
| 2007/0203435 A1* | 8/2007 | Novak .................. A61H 23/02 601/70 |
| 2007/0235716 A1 | 10/2007 | Delic et al. |
| 2008/0045775 A1* | 2/2008 | Lozano .............. A61N 1/36082 600/12 |
| 2008/0161883 A1 | 7/2008 | Conor |
| 2008/0195010 A1 | 8/2008 | Lai et al. |
| 2008/0208288 A1* | 8/2008 | Gesotti .............. A61N 1/36003 607/48 |
| 2009/0012436 A1 | 1/2009 | Lanfermann et al. |
| 2009/0133777 A1 | 5/2009 | De Antoni Migliorati |
| 2009/0189558 A1 | 7/2009 | Ford et al. |
| 2009/0190602 A1 | 7/2009 | Sung et al. |
| 2009/0201877 A1 | 8/2009 | Noh et al. |
| 2010/0057149 A1 | 3/2010 | Fahey |
| 2010/0081963 A1 | 4/2010 | Gilhuly |
| 2011/0082517 A1 | 4/2011 | Brezel et al. |
| 2015/0374985 A1 | 12/2015 | Fahey |
| 2016/0022481 A1 | 1/2016 | Fahey et al. |

FOREIGN PATENT DOCUMENTS

| | | |
|---|---|---|
| JP | 2002-052000 A | 2/2002 |
| JP | 2006-510431 | 3/2006 |
| KR | 10866543 B | 11/2008 |
| WO | WO-01/52759 A1 | 7/2001 |
| WO | WO-03/086217 A1 | 10/2003 |
| WO | WO-2004/089185 A2 | 10/2004 |
| WO | WO-2004/098703 A2 | 11/2004 |
| WO | WO-2005/075018 A1 | 8/2005 |
| WO | WO-2005/105203 A1 | 11/2005 |
| WO | WO-2007/017778 A2 | 2/2007 |
| WO | WO-2007/041540 A1 | 4/2007 |
| WO | WO-2007/046886 A1 | 4/2007 |
| WO | WO-2008/032282 A2 | 3/2008 |
| WO | WO-2008/034607 A1 | 3/2008 |

(56) References Cited

FOREIGN PATENT DOCUMENTS

| WO | WO-2008/075250 A1 | 6/2008 |
|---|---|---|
| WO | WO-2008/116232 A1 | 9/2008 |
| WO | WO-2009/009661 A1 | 1/2009 |

OTHER PUBLICATIONS

Bennie et al.; Toward the optimal waveform for electrical stimulation of human muscle; Eur J Appl Physiol; vol. 88; pp. 13-19; Nov. 2002.

International Search Report and Written Opinion Application No. PCT/US2009/049601, dated Feb. 9, 2010, 12 pages.

International Search Report and Written Opinion Application No. PCT/US2009/055089, dated Apr. 7, 2010, 9 pages.

Lacey et al.; Reductions in the amount of time spent in direct patient care by staff nurses in North Carolina; north Carolina Center for Nursing; Aug. 2002.

Lyons et al.; An investigation of the effect of electrode size and electrode location on comfort during stimulation of the gastrocnemius muscle; Medical Engineering & Physics; vol. 26; pp. 873-878; Dec. 2004.

Miklavcic et al.; Electrical Properties of Tissues; Wiley Encyclopedia of Biomedical Engineering; (year of publication is sufficiently earlier than the effective U.S. filing dated and any foreign priority date) 2006.

Morris, Peter E.; Moving our critically ill patients: mobility barriers and benefits; Critical Care Clinics; vol. 23; pp. 1-20; Jan. 2007.

Petrofsky et al.; Estimation of the distribution of intramuscular current during electrical stimulation of the quadriceps muscle; Eur J Appl Physiol; vol. 103(#); pp. 265-273; Jun. 2008.

Prausnitz, Mark R.; The effects of electrical current applied to skin; a review for transdermal drug delivery; Advanced Drug Delivery Reviews; vol. 18; pp. 395-425; Feb. 8, 1996.

Rafolt et al.; Dynamic force responses in electrically stimulated triceps surae muscles: effects of fatigue and temperature; Artificial Organs; vol. 23; No. 5; pp. 436-439; May 1999.

Snyder-Mackler et al.; Use of electrical stimulation to enhance recovery of quadriceps femoris muscle force production in patients following anterior cruciate ligament reconstruction; Phys Ther.; 74(10); 901-7; Oct. 1994.

Solomon et al.; The effects of TENS, heat, and cold on the pain thresholds induced by mechanical pressure in healthy volunteers; Neuromodulation; vol. 6; No. 2; pp. 102-107; Apr. 2003.

Stecker et al.; Mechanisms of electrode induced injury. Part 1: theory; Am. J. END Tech.; vol. 46; pp. 315-342; Dec. 2006.

Suganuma et al.; Measurement of Tension of tendon tissue based on electrical impedance; J. Ortho Science; vol. 9; pp. 302-309; (year f publication is sufficiently earlier than the effective U.S. filing date and any foreign priority date) 2004.

Zanotti et al.; Peripheral muscle strength training in bed-bound patients with COPD receiving mechanical ventilation: effect of electrical stimulation; Chest; vol. 124; No. 1; pp. 292-296; Jul. 2003.

\* cited by examiner (a)

(b)            (c)

SYSTEMS AND METHODS FOR AUTOMATED MUSCLE STIMULATION

CROSS-REFERENCE TO RELATED APPLICATIONS

This application is a continuation of U.S. application Ser. No. 15/091,494, filed Apr. 5, 2016, which is a continuation of U.S. application Ser. No. 14/532,595, filed Nov. 4, 2014, now U.S. Pat. No. 9,302,104, which is a division of U.S. application Ser. No. 13/647,249, filed Oct. 8, 2012, now U.S. Pat. No. 8,892,210, which is a continuation-in-part of U.S. application Ser. No. 12/497,230, filed Jul. 2, 2009, now U.S. Pat. No. 8,285,381, which claims priority to U.S. Prov. App. No. 61/133,777, filed Jul. 2, 2008, U.S. Prov. App. No. 61/189,558, filed Aug. 19, 2008, U.S. Prov. App. No. 61/190,602, filed Aug. 29, 2008, and U.S. Prov. App. No. 61/201,877, filed Dec. 15, 2008; all of which are incorporated herein by reference in their entireties.

Application Ser. No. 13/647,249 also claims priority to U.S. Prov. App. No. 61/544,113, filed Oct. 6, 2011, incorporated herein by reference in its entirety.

BACKGROUND

Neuromuscular electrical stimulation (NMES) (also referred to as powered muscle stimulation, functional muscle stimulation, electrical muscle stimulation, and other terms) is an established technology capable of activating a person's muscles involuntarily and non-invasively. NMES is typically delivered as an intermittent and repeating series of short electrical pulses. A complicating factor is that each person responds differently to NMES. Thus, it is often required to adjust stimulation parameters on a case-by-case basis to ensure that a person receives effective therapy that is both safe and well-tolerated. During adjustment for traditional NMES, a trained operator must be present to guarantee that stimulation parameters remain within a safe range of values. Even with a trained operator, parameter adjustment to achieve optimal results is typically an iterative and time-consuming process.

Zanotti and colleagues (Chest 124:292-296, 2003), incorporated herein by reference, have demonstrated improved functional outcomes and accelerated patient rehabilitation by applying NMES to the leg muscles of bed-bound COPD patients. Despite this and other clinical evidence showing improved patient outcomes, NMES technology has not been transferred for use in the intensive care unit (ICU) setting (where critically ill patients are cared for), although it has been hypothesized that doing so could improve patient care (Morris et al., Critical Care Clinics, 23:1-20, 2007—incorporated herein by reference). In its current state, NMES is inadequate for use in the ICU setting.

Two major factors provide a barrier to the use of NMES in the ICU: 1) the need for user training for safe and effective delivery of therapy and 2) the labor-intensive nature of current NMES devices. Most FDA-approved electrical muscle stimulators are designed for use in more than one application (ex. pain management, sports rehabilitation, muscle atrophy), and therefore leave many stimulation settings described above under the control of the operator (ex. a nurse, physical therapist). Virtually all nurses, as well as most physical and occupational therapists, are not trained to deliver NMES therapy and therefore do not have the knowledge base required to adjust stimulation parameters safely and effectively or to tailor energy levels on a patient-by-patient basis. A second muscle stimulation task requiring training involves placement of stimulation electrodes over the motor points of muscles. With traditional NMES, precise electrode placement is required if muscles are to be activated effectively in a manner such that the person receiving therapy experiences minimal discomfort. Current methods to determine electrode placement involve initial estimations based upon anatomical markers, followed by iterative trial-and-error based adjustments based upon an observed muscle response. Again, most nurses and physical therapists are not trained to perform these adjustments.

The second barrier to the use of NMES in the ICU is the lack of available personnel to deliver therapy. Even if current electrical stimulation devices were straightforward to use, stimulation electrode re-positioning and stimulation parameter adjustment is a labor-intensive activity. A recent study (Lacey et al., North Carolina Center for Nursing, 2002—http://www.nursenc.org/research/chgs_time_al-loctn.pdf), incorporated herein by reference, found that time for direct patient care by nurses declined by 6% during the period of 1999-2001. Given skyrocketing health-care costs, many institutions cannot afford or cannot justify hiring additional help, especially well-compensated advanced operators trained in delivering NMES therapy. In particular, critical care nurses have their time fully committed, and cannot take on a new patient care activity without discarding another. Because NMES is not vital to a critically ill person's immediate survival, it's delivery would need to be very time-efficient in order for it to be implemented in the ICU setting. Existing electrical muscle stimulation devices found in the prior art do not meet this standard.

Within the ICU, the patient cohort comprised of sedated, comatose, or otherwise non-interactive patients poses unique challenges that further render existing electrical stimulation devices and treatment paradigms ineffective. Because patients are non-interactive, direct patient assessment of muscle contraction strength (often used to aid judgments of stimulation effectiveness) is unavailable. This leaves the onus of judgment to a device operator who is most often left with only visual evidence of contraction (i.e., looking for muscle and/or body part movement in treated regions). A striking example of the effect of this limitation arises if the target muscle group for stimulation is the quadriceps. As the overwhelming majority of sedated or comatose ICU patients lie in bed with legs extended, little to no physical movement is activated by stimulating quadriceps muscles, even though the process of stimulation is effectively preserving muscle mass and strength. Particularly in older patients with low baseline muscle mass, induced muscle contractions may be very difficult to distinguish visually. These difficulties exacerbate problems related to a modality that is already riddled with shortcomings.

Furthermore, although generally considered safe, NMES therapy is occasionally associated with skin and/or tissue burns. There are multiple potential causes of burns. One common cause is an excessive amount of current flowing through a small area of tissue (i.e., large current density). While the risk of this type of burn can be minimized through the use of large dispersive electrodes and mechanisms to ensure good electrode contact with a person's skin, burns of this type continue to occur. Another type of burn is associated with abnormally large temperature increases in the electrode itself, oftentimes due to an electrode malfunction. In this scenario, increases in electrode temperature may result in superficial skin burns, or more serious burns if the situation is not addressed. Over time, temperatures at the skin surface may also increase when using normally functioning electrodes simply due to resistive heating in skin, although in this scenario temperatures rarely reach dangerous levels. Stecker and colleagues (Am J END Tech., 43:315-342, 2006), incorporated herein by reference, provide an extensive review of the potential mechanisms of injury when using electrical skin electrodes.

Temperature control requirements during NMES seek to constrain temperatures within a range that is safe to avoid tissue burns. As noted by Prausnitz (Advanced Drug Delivery Reviews 18:395-425, 2006), incorporated herein by reference, the required temperature rise for tissue damage is a function of the duration which the temperature rise is applied to tissue. For surface electrodes, temperature rises are generally desired to be less than 6° C. during NMES therapy. Given that average baseline skin surface temperatures generally do not exceed 33° C., it is desirable that temperatures above 39° C. should be avoided.

For most users, the risk of serious skin or tissue burn due to an abnormally hot electrode or a severe temperature rise at the skin interface is minimal. This is because the electrode can be removed or the NMES system disabled by the user before temperature rises become significant. For example, most persons receiving NMES would detect a painful or unpleasantly hot temperature shortly after an electrode malfunction (as the electrode begins to warm) and would be able to terminate therapy (or inform a trained operator that something is wrong) before temperatures continued to rise to more serious levels. In this scenario, minor skin irritation or skin burns could occur, but more serious skin or deep tissue burns are avoided.

Immobilized persons, however, are at increased risk for serious skin and deep tissue burns. A large proportion of immobilized persons are medical patients who are suffering from conditions such as coma or who are receiving interventions (such as mechanical ventilation) that generally require sedation and/or analgesia. These patients are likely to have abnormal skin sensation and/or a reduced sensory threshold. As a result, these patients have a reduced capacity to acknowledge that an electrode or region of skin is increasing in temperature. Thus, the risk mitigation mechanisms described above that exist for most users are not available to these persons. Accordingly, the U.S. FDA places a labeling requirement on marketing literature for powered muscle stimulators, indicating that caution must be utilized when electrodes are placed over skin areas lacking normal sensation.

The potential for severe burns is one of the major reasons that NMES therapy is not typically delivered to comatose, sedated, or analgesed patients in the intensive care units (ICUs) of most hospitals. Recent peer-reviewed medical literature has confirmed the potential benefits of NMES for immobilized ICU patients. However, in these very ill patients, the consequences of a serious burn (and subsequent risk of further infection, etc) are potentially devastating. Given that the focus of ICU care is to maintain life and stabilize a patient's vital signs, the risk of harmful burns outweighs any downstream benefits related to the maintenance of muscle strength. In the high demand environment of the ICU, a nurse or other care provider does not have the time or resources to constantly check stimulation electrodes to ensure proper functioning and a safe range of operating temperatures. Existing electrical stimulation devices do not provide adequate protection against burns when used with this vulnerable group of persons.

Therefore, a need exists for improved NMES systems and methods, which may be delivered to comatose, sedated, or analgesed subjects.

SUMMARY

The invention provides systems and methods for neuromuscular electrical stimulation to muscle and/or nervous tissue. Various aspects of the invention described herein may be applied to any of the particular applications set forth below or for any other types of electrical stimulation and sensing systems or methods. The invention may be applied as a standalone system or method, or as part of an integrated medical treatment system. It shall be understood that different aspects of the invention can be appreciated individually, collectively, or in combination with each other.

Detailed within are systems and methods for delivering NMES to a critically ill person or other person who is sedated, comatose, or has abnormal skin sensation globally or locally. A logical extension of the systems and methods would also prove beneficial for applying NMES to healthy persons or persons with non critical care medical conditions. Also disclosed is an example system that would empower the use of an NMES method. The method allows for an operator not trained in NMES to deliver safe and effective electrical stimulation therapy to a person. The method also enables NMES therapy to be delivered in a time-efficient manner in environments, such as a hospital ICU, that are incompatible with most labor-intensive procedures.

An NMES method may include several steps intended to provide performance, ease of use, and safety improvements over technology known in the prior art. One step involves placing an array of stimulation electrodes in contact with a patient's skin in the vicinity of muscles it is desired to stimulate. A later step involves using a device that communicates with the array to automatically optimize the electrical stimulation parameters, the location of stimulus application, or both. Following optimization, safe and effective NMES may be initiated automatically without requiring additional involvement of the operator.

In an example scenario, the operator begins by using imprecise estimates to place adhesive pads containing a number of stimulation electrodes and sensing element(s) on a person's skin in the region of the target muscle(s) and the mechanically connected tendon. This array of electrodes may be connected to a control unit comprising components such as a signal generator, memory, processor, and power supply. When activated, the system may generate stimulating signals described by variable parameters that may be optimized based upon the feedback from the sensing components. Parameters that may be optimized include anatomical location of the applied stimulus, amplitude of stimulus, shape of stimulus waveform, duration of stimulus signal, and stimulus signal frequency. The operator may only be required to place the electrode array and activate the control unit in order to initiate safe and effective therapy. After a specified amount of time, the control unit shuts down automatically so that the operator does not have to be present to terminate therapy at the desired time. Given this method, NMES therapy may be delivered effectively by an untrained operator in a manner that requires very little effort and/or time.

In one embodiment of the system, the stimulating parameters can be optimized as follows: An electrical stimulus signal, described by a default set of stimulation parameters, may be delivered to the stimulating electrodes. The stimulating electrodes may be utilized to couple the generated stimulus to underlying muscles and/or nerves, causing the muscle(s) to contract. In such a manner, the stimulating electrodes may be in electrical contact with underlying muscle and/or nervous tissue. Simultaneously, the sensing components may detect signals that are representative of the electrical properties of the tendon, the geometric path of current flow, the electrical stimulus coupled to the body by the stimulation electrodes, and other factors. The sensing components may deliver these signals to the control unit, which stores them for later comparison. The stimulus parameters can be cycled through a series of predetermined settings, and this process may be repeated. The control unit may then compare the signals recorded by the sensing components under different stimulation conditions in order to determine optimal settings for the stimulation parameters. Several optimization algorithms may be utilized depending on the outcome that is desired to achieve.

The method described may be useful because it eliminates the need for an operator to be trained in NMES in order to deliver safe and effective electrical stimulation therapy. As described previously, surface electrode placement and electrical stimulation parameter selection can be non-intuitive and time consuming for even trained operators. No method, system, or device described in the prior art allows for an inexperienced operator to deliver optimal NMES therapy to non-interactive persons. The method described in this document may expand the use of NMES therapy into facilities where trained NMES operators are not available. The current method may also increase the efficiency of trained operators by simplifying the NMES procedure and decreasing the optimization and setup time required to deliver safe and effective therapy.

The system described in this document may be useful because it is an example of a system that would empower the described method to be utilized. The system may also allow for non-invasive determination of muscle contraction strength, tendon tension, and other parameters, making it useful as a stand-alone system independent of the described method. Key features of the system may include the use of a selectively-activated array of surface electrodes, muscle sensor(s) and feedback mechanism(s), and automated optimization algorithms in the control unit. The array of surface electrodes allows for imprecise placement of the stimulation pad, eliminating the need for iterative stimulation electrode adjustment in order to optimize the efficacy of the delivered energy. The control unit could use measurements from both the stimulation electrodes and sensing element(s) to automatically select which stimulating electrodes in the array should be active for a given person and stimulation pad placement. Similarly, information from the sensing element(s) is used to automatically optimize the electrical stimulation parameters used to produce muscle contraction. This rapid optimization may ensure that safe and effective therapy is delivered to the person without requiring a trained NMES operator to adjust parameters manually. The optimization algorithm also introduces quantitative criteria into the process of selecting stimulation parameters, eliminating qualitative and subjective measures of performance and removing the significant intra-operator variability associated with the devices described in the prior art.

The presently described method and system has several benefits: 1) It provides a novel approach to feedback-based NMES optimization that will be more robust for use with obese, edematous, and other persons, 2) It takes advantage of stress-induced electrical property changes in tendon tissue to improve performance relative to other methods of NMES optimization found in the prior art, 3) It has been designed such that it may be used for therapy in persons that may be located in a hospital setting and may be very ill, 4) It has been designed so that it is safe to use in critically ill individuals, 5) It has been designed such that physician access to vital anatomy (such as major vessels for catheter placement) is not compromised, and 6) Any components of the presently described system that come in direct contact with the person receiving therapy are designed such that they are disposable and/or sterilizable.

Also detailed within are a device, system, and method for automatically preventing skin or deep tissue burns in persons receiving NMES. Use of the device, system, and method will decrease the risk profile of NMES use in critically ill, sedated, or comatose patients and allow for more patients to benefit from this therapy. The device and system will enable NMES therapy to be routinely delivered in persons with abnormal skin sensation without fear of inflicting burns or other side effects associated with abnormally high operating temperatures. Specifically, the device and system will enable NMES therapy to be automatically terminated in the event of potentially dangerous increases in temperature local to the stimulation site. In this scenario, a person receiving NMES therapy and/or the medical care provider (if applicable) would not need to actively disable the stimulation device if unsafe operating conditions are encountered. Implementation of the method will allow for safer application of NMES to persons who are vulnerable to tissue burns.

The device and system may include two main components: an electrical stimulation pad and a 'smart' control unit that contains microprocessor or other control elements that can both generate a waveform/signal for NMES therapy and also execute safety measures in response to signals received from electronics and/or sensors in the pad. The pad may contain two or more stimulation electrodes as well as temperature sensitive elements that are capable of measuring either absolute or relative temperatures. Connecting the pad and the control unit may be a means for transmitting and receiving electrical signals, such as NMES waveforms and data signals produced by temperature sensitive elements. The connection means could be a standard cable connection, a wireless connection such as Blue-tooth, WiFi, infrared, or other similar connections.

As an example of the usefulness of the device, system, and method, consider the following example medical scenario: The stimulation pad is placed on a desired skin region of a comatose patient by a care provider. Once the pad is secured, NMES therapy is initiated by the provider by performing the appropriate actions on the control unit. At this point, the care provider returns his or her attention to their other patient care activities. Sometime during the NMES therapy session, patient or equipment conditions change in a way that affects system operation (ex. an electrode malfunctions, patient incontinence makes stimulation region wet/moist, excessive sweating changes skin conditions). Skin regions near the stimulation electrodes (or the stimulation electrodes themselves) begin to rise in temperature and very quickly approach unsafe levels. Temperature sensors in the pad, in the electrodes, or both record this rise in temperature and send signals to the control unit, which automatically terminates NMES therapy. In this case, serious burns and pain to the patient are avoided. Contrast this scenario to the situation where a conventional NMES device is used: without a warning or safety system in place, a care provider would likely not notice an unsafe operating condition until significant tissue damage had occurred.

The device and system are useful because when implemented they will allow for NMES therapy to reach a new subset of persons. For example, it is well described in the medical literature that comatose patients or patients who are sedated for extended periods of time suffer tremendously from the effects of muscle atrophy. NMES therapy is known to prevent or retard muscle atrophy. Despite this, NMES has found extremely limited use in this patient population. A major reason for this is the belief that burns, although rare, would prove devastating to these very ill patients. Additionally, these patients may have abnormal skin sensation and may be non-interactive/communicative, placing them at increased risk for serious burns. A device or system that could provide an extra layer of protection against burns would tilt the cost-benefit ratio in the favor of delivering NMES therapy. Thus, the device and system described herein will allow for a greater number of persons to receive the benefits of NMES therapy. The device and system are also useful for use in non-sedated or comatose persons. For these users, the device and system could be used to terminate NMES therapy earlier than a person may do so on their own, helping to avoid even minor burns. Thus, use of the device and system will reduce the incidence of burns in the general use population.

The presently described device and system have a number of benefits, including: 1) They allow for improvements in the safety and efficacy of patient care, 2) They allow an existing therapy to be applied safely to a new patient group to treat a terrible problem with limited existing interventions, and 3) Effective use does not require extensive operator interaction or decision making, and will not increase care provider workload.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Stimulation and Sensing Electrodes within Same Pad

Figure 1:
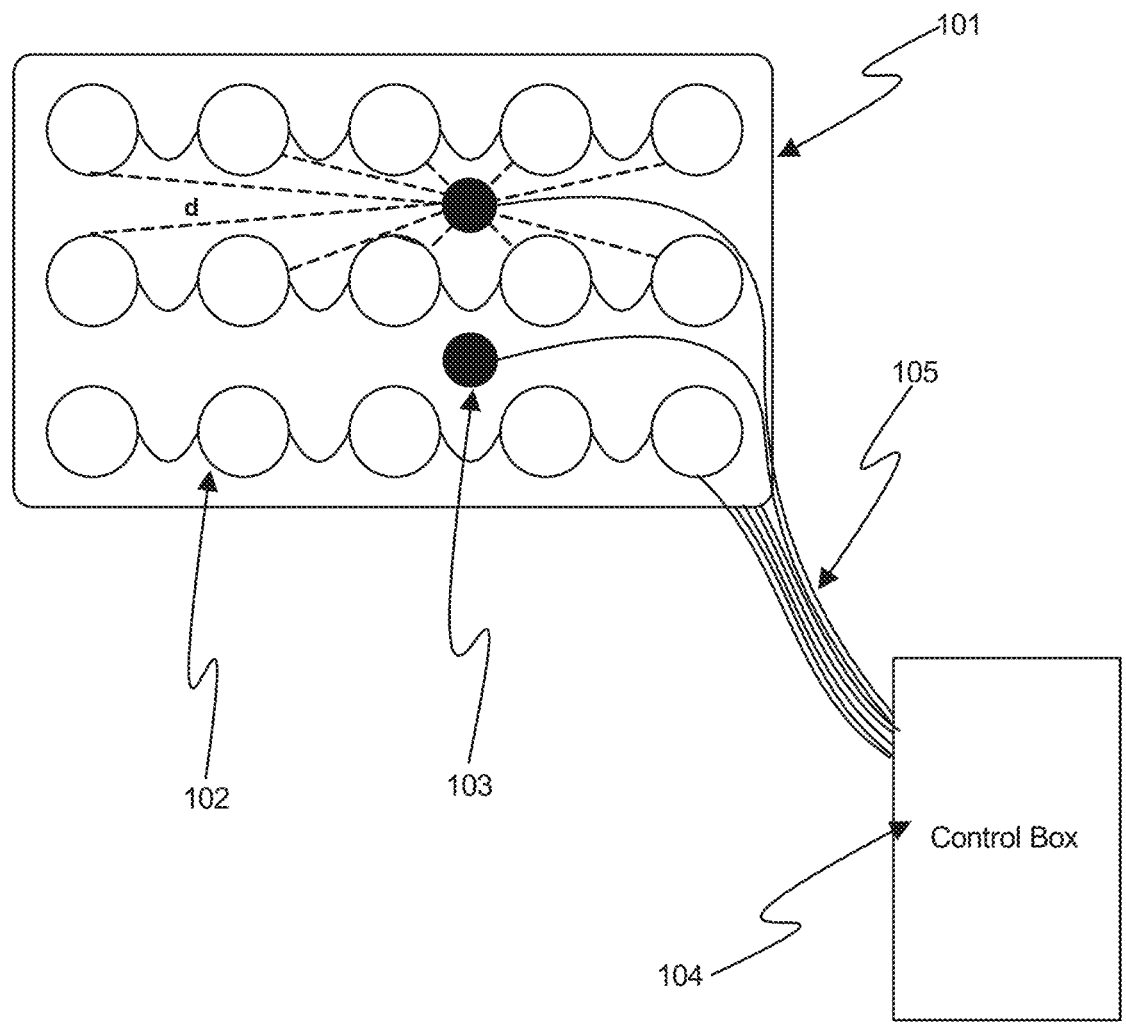
FIG. 1 provides an overview of a neuromuscular electrical stimulation (NMES) system in accordance with an embodiment of the invention.

FIG. 1 shows, in accordance with an embodiment of the invention, an array of electrodes placed within a thin, flexible housing 101. The thin flexible housing may be connected to one or more stimulating electrode 102 and/or one or more sensing electrode 103. A control box 104 may be electrically connected to the one or more stimulating electrode and/or the one or more sensing electrode. The control box may communicate with the electrodes through a series of wire connections 105. The system may be used for neuromuscular electrical stimulation (NMES) of muscle tissue.

In a preferable embodiment of the invention, the thin, flexible housing 101 may form a substrate or support for an electrode pad. The thin flexible housing may be formed of a material that may enable the pad to conform to an anatomical placement on a subject. For example, the housing may include a deformable or elastic component. The placement of the pad may determine which muscle tissue of the subject may be stimulated by the NMES device. For instance, the muscle tissue proximate to the pad may be stimulated.

The one or more stimulating electrode 102 may be mechanically attached or integrated into the pad 101. In a preferable embodiment, an array of stimulating electrodes may be provided on the pad. Any number of electrodes may be provided on the array. For example, an array may be formed of n rows and m columns, where n and m are any integer with a value of one, two, three, four, five, six, seven, eight, nine, ten, or greater. In other embodiments, the array of stimulating electrodes need not be arranged into rows and columns and may have any placement on a pad.

Sensing electrodes 103 may be located near the center of the stimulating electrode array 102. For example, one, two, three, four, or more sensing electrodes may be placed near the center of the pad 101. However, sensing electrodes may be placed anywhere on the pad, and need not be at the center. For example, the sensing electrodes may be distributed substantially even over the surface of the pad, between any of the stimulation electrodes, along the border of the electrodes, or beyond the area defined by the stimulation electrodes. Optionally, the sensing electrodes may be distributed so that they fall within the array of electrodes, and not outside an area defined by the array of electrodes. Similarly, any number of sensing electrodes may be provided.

In some embodiments, a sensing electrode may function as a reference electrode. The reference electrode may be positioned such that the reference electrode is at a predetermined distance or range of distances from the stimulation electrodes. Also, the reference electrode may be positioned to be at a predetermined distance or range of distances from other sensing electrodes. In some embodiments, the reference electrodes may be at a greater distance from the stimulation electrodes than other sensing electrodes are from the stimulation electrodes. Thus, a reference electrode may be further from stimulation electrodes than other sensing electrodes. In some embodiments, the reference electrode may be at a distance or relative position from the stimulation electrodes such that the effects of the stimulation electrodes on the signals picked up by the reference electrodes are reduced, minimized, or non-existent.

The control box 104 may contain pulse generation electronics as well as digital and/or analog signal processing components. The control box may provide electrical stimulation signals to a stimulation electrode 102 and/or receive signals from a sensing electrode 103. In preferable embodiments, the signals provided to the stimulation electrode may depend on signals received from the sensing electrode. Thus, the system may provide a feedback, to control the electrical stimulation provided.

In some embodiments, each of the stimulation electrodes may be individually controllable by the control box. For example, the stimulation electrodes may be connected to the control box in such a way that for each stimulation electrode, whether any stimulation is provided, the level of stimulation provided, or pulse width, duration, frequency, amplitude, waveform, or any other characteristic of the stimulation provided to the stimulation electrode may be individually controlled by the control box. Thus, customization and localization of stimulation may be closely controlled. See, e.g., PCT Publication No. WO 2007/017778 and PCT Publication No. WO 2005/075018, which are hereby incorporated by reference in their entirety.

There may be a number of parameters that describe the stimulation electrical pulses. As previously mentioned these include voltage amplitude, current amplitude, waveform shape (e.g., square, sinusoidal, exponential, monophasic/biphasic, symmetric/asymmetric), pulse length, pulse repetition frequency, and the relative on/off times between repeating series of pulses. Depending on the mode of operation (e.g., constant current vs. constant voltage stimulation), some of these parameters may be independently user-controlled, while others are dependent on external factors such as the electrical impedance between electrodes.

There may also be several stimulation parameters that are typically operator-controlled. The values of these parameters directly impact the safety, efficacy, and relative comfort of an electrical stimulation therapy session. For example, stimulation pulse length and waveform shape have been shown to significantly impact comfort and tolerability. Pulse repetition frequency and voltage/current amplitude are correlated with strength of muscle contraction and thus treatment efficacy. Current density, a function of injected charge, must be carefully controlled to avoid burns, nerve injury, and other potential complications (as detailed by Prausnitz Advanced Drug Delivery Reviews 18:395-425, 2006 and Stecker et al Am J END Tech., 43:315-342, 2006, both of which are incorporated herein by reference). Additional parameters may impact other features of NMES therapy, including the required duration of therapy and the suitability for use in certain patient populations.

In some other embodiments, subsets of the stimulation electrodes provided may be controlled. For example, if three subsets of stimulation electrodes are provided, each of the electrodes within the same subset may receive the same stimulation (or lack thereof). Thus, for example, the first subset may lie dormant and not receive any stimulation, the second subset may receive a stimulation of a high amplitude and great frequency, and the third subset may receive a stimulation with a lower amplitude and lesser frequency.

In an alternate embodiment, all of the stimulation electrodes on a pad may receive the same stimulation.

Similarly, signals from the sensing electrodes may be individually analyzed, or partially aggregated and then analyzed, or completely aggregated and analyzed. The control box may perform signal processing steps to the signals from the sensing electrodes, examples of which are to be discussed in greater detail below.

Wire connections 105 may enable the control box 104 to communicate with the electrodes. In some alternate embodiments, the stimulation and/or sensing electrodes may be able to communicate with the control box wirelessly.

In accordance with an embodiment of the invention, an NMES system may be provided for electrically stimulating a selected muscle-tendon region. In some instances, a muscle-tendon region may include a muscle group. A muscle-tendon region may also refer to a general region encompassing a muscle group and associated tendons. The NMES system may be provided for electrically stimulating a targeted muscle and/or nervous tissue. Any description of an NMES targeted region or tissue may also refer to any other type of NMES targeted region or tissue.

In some embodiments, an integral electrical stimulation unit, which may include at least one stimulating electrode and at least one sensing electrode may be provided. The integral electrical stimulation unit may be unitary and provided as one piece. The stimulating electrode and the sensing electrode may be integrated within a substrate or pad. The integral electrical stimulation unit may be provided so that a plurality of sensors are positioned within an array of stimulating electrodes. The plurality of sensors may be positioned so that they fall between stimulating electrodes and/or are within an area defined by the array of stimulating electrodes.

The position of the stimulating electrodes may depend on target muscle and/or nervous tissue. The stimulating electrodes may have contact portions that are positioned on the skin over the target muscle and/or nervous tissue. The stimulating electrodes may be in electrical contact with the underlying target tissue, even if they are not in direct physical contact with the tissue. Thus, the stimulating electrodes may be able to electrically communicate with target tissue transdermally.

Each stimulating electrode may be a predetermined distance from a sensing electrode. For example, in some embodiments, the position of a stimulating electrode may be selected to be a predetermined distance from the sensing electrode. For example, in forming the integral electrical stimulation unit, a desired distance d or relative position of the stimulating electrodes relative to one or more sensing electrodes may be calculated, and the electrodes may be positioned accordingly. In some embodiments, the placement of each stimulating electrode may be predetermined to fall within a spaced apart distance from a plurality of sensors. In some embodiments, a desired range of distances may be provided, where electrodes may fall within that distance range from the plurality of sensors.

In some embodiments, the predetermined distance d or desired distance range for the electrodes from the sensors may depend on the target muscle-tendon region. Based on the underlying target anatomy, desired placements of the stimulating and sensing electrodes may be determined and/or calculated, and the integral electrical stimulation unit may be formed accordingly.

In some embodiments, one or more sensor may be a reference sensor. A reference sensor may also be a predetermined distance or desired distance range from the electrodes. In some instances, the distance of a reference sensor from the electrodes may be greater than the distance between the other sensors and the electrodes. The position of a reference sensor may be predetermined or predefined depending on the expected anatomical features.

The NMES system may also include a controller which may be in electrical communication with the stimulating electrodes and sensing electrodes of an integral electrical stimulation unit. The controller may provide electrical signals to the array of electrodes based on electrical signals received from the plurality of sensors. In some instances, the controller may provide electrical signals to a subset of the stimulating electrodes in the array of stimulating electrodes based on instructions from the controller.

Figure 2:
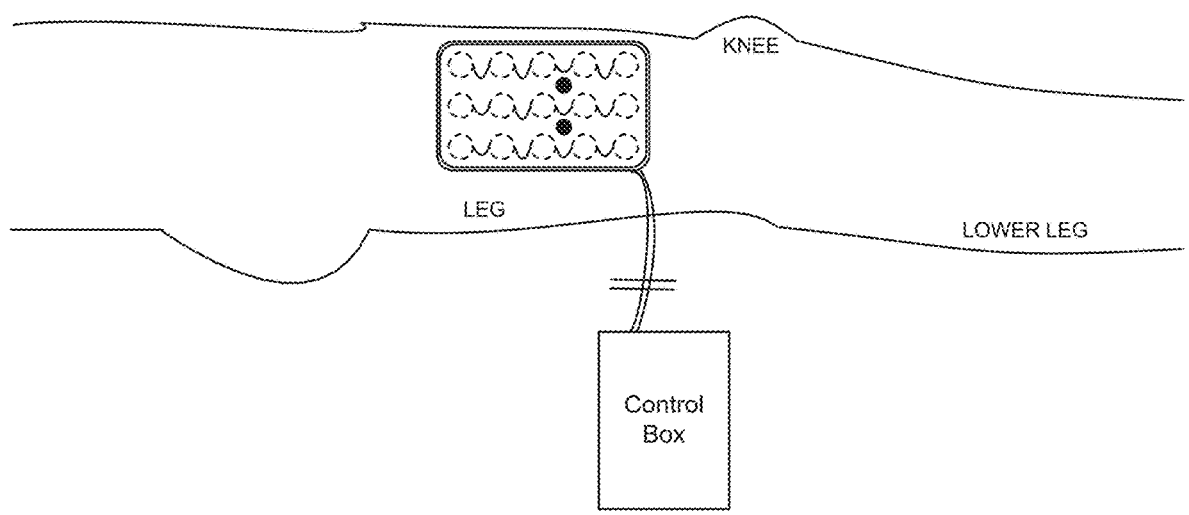
FIG. 2 provides an example of how an NMES method and system could be used.

FIG. 2, provides an example of one potential anatomic placement of the embodiment described in FIG. 1. For instance, a pad may be placed on the front of the thigh of a subject, which may result in electrical stimulation of quadriceps. The pad may be placed above the knee of the subject. The pad, which may include stimulation electrodes and/or sensing electrodes may contact the skin of the patient. Electrical stimulation signals may reach the underlying muscle and/or nervous tissue transdermally. Thus, since electrical conduction may be provided from the stimulation electrode to the underlying tissue, the stimulation electrode may be in electrical contact with the underlying tissue.

In other implementations, the pad may be placed at another location on a patient. For example, the pad may be used to stimulate other leg muscles, or muscle and/or nervous tissue provided in a subject's arms or torso. For example, the pad may be placed at the rear of the thigh of a subject, around an entire thigh of the subject, in the front of back of the power leg of the subject, at the upper arm of a subject, at the lower arm of a subject, at the waist of a subject, at the upper torso of a subject, or below the waste of a subject.

Figure 3:
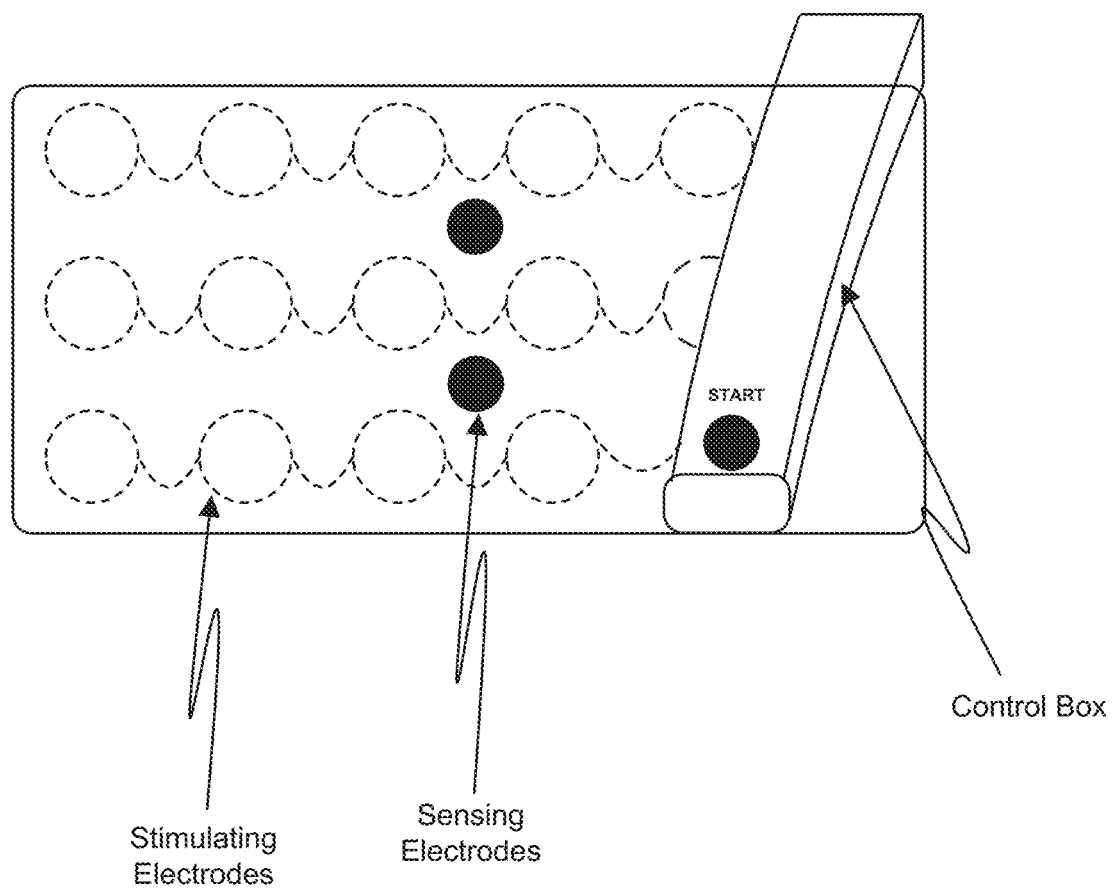
FIG. 3 shows an example of how a control unit may be integrated with an electrode array.

FIG. 3 shows an embodiment where the electrode array and the control box are comprised within a single unit. For example, a thin, flexible housing may be provided, which may act as a substrate or support for the unit. The thin, flexible housing may form a pad for the unit. One or more stimulating electrodes and/or one or more sensing electrodes may be provided on the flexible housing. A control box may also be provided on the housing, to form the single unit. Preferably, electrical connections between the stimulating electrodes and/or sensing electrodes with the control box may be provided by wires that may be integrated into the single unit.

The control box may be affixed to the pad of the unit. In some embodiments, the control box may be integrally connected to the pad of the unit so that it may not be removed. In other embodiments, the control box may be removably attached to the pad of the unit. For example, the control box may snap into and out of a connection provided on the unit, may be velcroed to the unit, may be clipped or clamped to the unit, or may be removably attached to the unit in any other manner. Removable or fixed control units may electrically communicate with the rest of the unit via wire or wireless connections.

Figure 4:
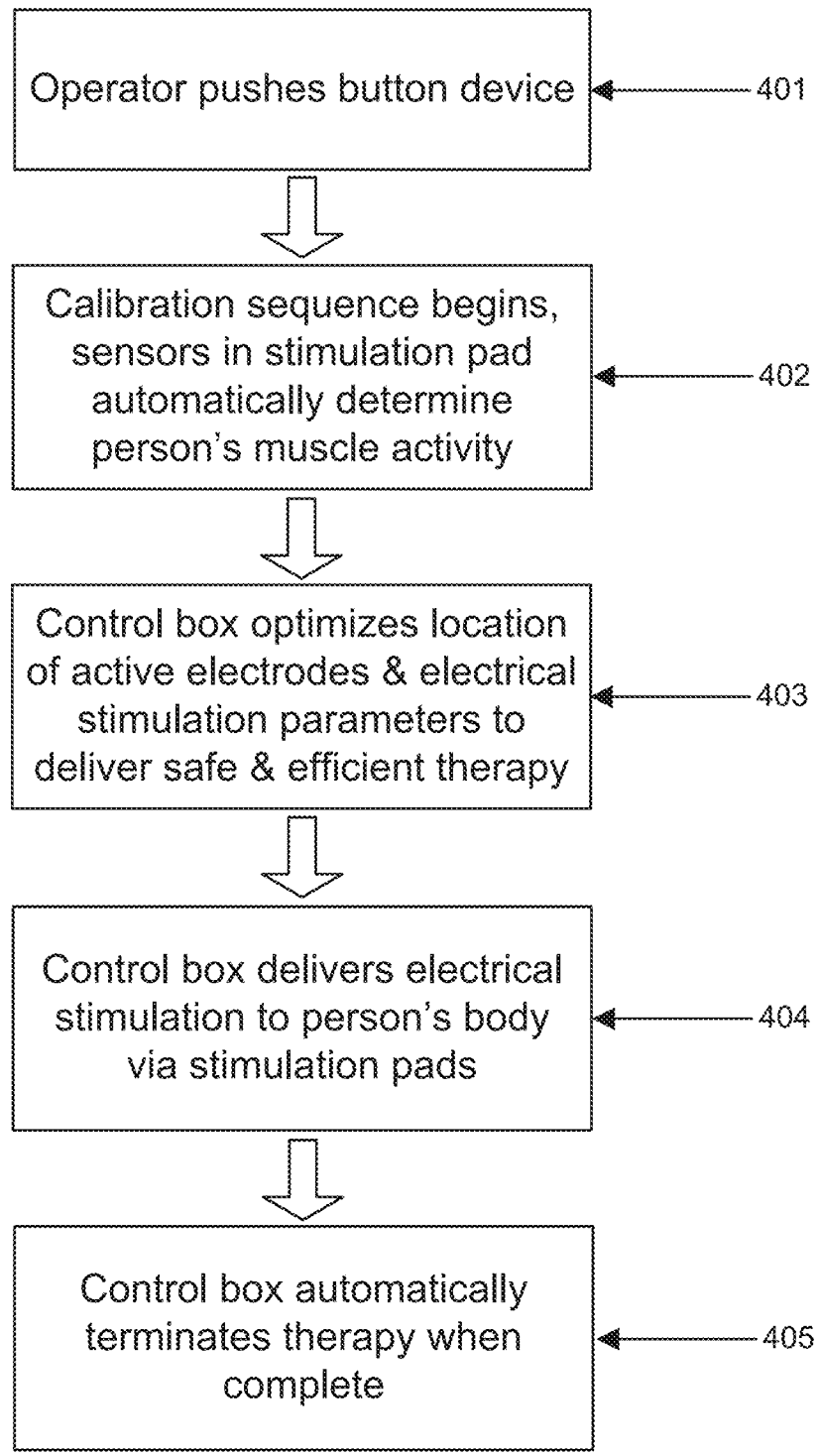
FIG. 4 shows a flow chart illustrating a possible series of steps that may occur during an NMES method.

As shown in FIG. 4, a preferable embodiment of the described method could be described by a simple flow chart. For example, a method of performing NMES may be provided where the method may include an operating pushing a button device 401, beginning a calibration sequence, where sensors in a stimulation pad may automatically determine a person's muscle activity 402, optimizing a location of active electrodes and electrical stimulation parameters to deliver safe and efficient therapy 403, delivering an electrical stimulation to a person's body via one or more stimulation pad 404, and terminating therapy when complete 405.

Only the first step 401 may require effort on the part of the operator. The subsequent steps 402-405 may be automatically implemented though algorithms executed by the control box.

During a method of NMES, an operator may place a stimulation pad on a desired anatomical region of a subject. The subject may be a patient, such as a comatose, sedated, analgesed patient, or a patient at the ICU, or may be a clinical test subject, or any other human, mammal, or any other animal that may receive NMES.

In a preferable embodiment, the operator may place the stimulation pad at an estimated location to stimulate the target muscle tissue, without having to place it at a precise location. The operator may place the stimulation pad to contact the skin approximately over the target muscle tissue. The stimulation pad may be attached to the skin using an adhesive or straps, or any other mechanism that may enable the stimulation pad to remain in contact with the skin. Once one or more stimulation pad is secured at the desired locations, an operator may activate the stimulation pad. The operator may initiate the activation by interfacing with a control box, such as by pushing a button device 401, or flipping a switch, touching a touchscreen, or performing any other such action that may enable the operator to initiate action through the control box.

Once it receives instructions to begin, the control box may begin a calibration sequence 402. The calibration sequence may include providing stimulation signals to one or more stimulating electrode and/or receiving signals from sensors of the stimulation pad. In some embodiments, the calibration sequence may include providing signals to stimulating electrodes in accordance with a predetermined sequence and at predetermined waveform characteristics. Alternatively, the calibration sequence may include providing signals to stimulating electrodes based on signals received from sensors. The signals received from the sensors may be analyzed by the control box to determine the subject's muscle activity.

The control box may optimize a location of active electrodes and electrical stimulation parameters to deliver safe and efficient therapy 403. For example, based on analysis performed during the calibration sequence, electrodes may be selected to provide electrical stimulation to target muscle tissue. Such electrodes may be a subset of the stimulating electrodes provided on the stimulation pad. In some embodiments, the selected electrodes may remain the same throughout the therapy. In other embodiments, the selected electrodes may vary over the course of therapy. Such variation may depend on signals provided by sensors in the stimulation pad, or may be predetermined based on the calibration sequence. In addition to variation of selected stimulating electrodes, variation may be provided to parameters of the applied stimulus. Thus, parameters that may be optimized include anatomical location of the applied stimulus, amplitude of stimulus, shape of stimulus waveform, duration of stimulus signal, and stimulus signal frequency. See, e.g., U.S. Pat. Nos. 4,838,272, 6,324,432 and 7,499,746, which are hereby incorporated by reference in their entirety.

The control box may deliver an electrical signal which may cause delivery of electrical stimulation to the subject's body via one or more stimulation pads 404. The electrical stimulation provided to the subject body may depend on algorithms performed by the control box to determine optimized parameters. For example, if the control box determines that an increased stimulation frequency is desirable, the stimulation pads may deliver electrical stimulation to the subject's body at an increased stimulation frequency.

The control box may automatically terminate therapy when it is complete 405. The control box may determine that therapy is complete based on predetermined instructions. For example, the therapy may be complete after a predetermined amount of time has elapsed, or after a predetermined amount of electrical stimulation has been provided. Alternatively, the control box may determine that therapy is complete based on signals received from the sensors. For example, the therapy may be complete when the sensors reach a particular threshold for an electrical signal.

In accordance with another embodiment of the invention, a method of electrically stimulating a selected muscle-tendon region of a body may be provided. The method may include placing a stimulation assembly in electrical contact with muscle tissue, wherein the stimulation assembly may be formed with a plurality of electrodes and at least one sensor. The sensor may be positioned at a predefined range away from each electrode to monitor the remote effects of electrical stimulation from the electrodes on the selected muscle-tendon region of the body.

In some implementations, the predefined range of distance for each electrode may be determined prior to forming the stimulation assembly. For example, prior to manufacturing or building the stimulation assembly, it may be desirable to calculate the predefined range of distance, and place each electrode and sensor within the stimulation assembly accordingly. In some embodiments, the predefined range of distance may depend on the anticipated anatomical placement of the stimulation assembly, while in other embodiments, the predefined range may be placement agnostic.

The method may also include receiving a feedback signal from at least one sensor of the stimulation assembly, and providing an electrical stimulation signal to at least one of the plurality of stimulation electrodes based on the received feedback signal.

Stimulation and Sensing Electrodes in Separate Pads

In a preferable embodiment, an NMES system may be comprised of two main functional components: a stimulation unit comprising an array of stimulation electrodes and sensor element(s) and a control unit. In a preferable embodiment, the stimulation unit may be comprised of two separate pads that can contact a person's body: a stimulation pad containing an array of stimulation electrodes and associated electronics, and a sensing pad containing muscle sensors and associated electronics. Alternatively, the stimulation pad and sensing pad may be composed of a single unit, or the two pads may be connected mechanically through straps, buttons, hooks, or other suitable means. The control unit may communicate with the stimulation unit through a wired connection, radiofrequency transmission, optical, acoustic, or electromagnetic signals, or another suitable mechanism. The control unit may be a separate unit that may be located some distance from the person receiving therapy. In an alternate embodiment, the control unit may be integrated into a housing unit containing the stimulating electrode and sensing component(s).

In some alternate embodiments of the invention, the stimulation pad and the sensing pad may be integrated into one piece. For example, the stimulation pad comprising stimulation electrodes and the sensing pad comprising sensors may share a common substrate. The stimulation pad and the sensing pad may be distinct regions on the common substrate or may be placed on a common substrate.

Any of the components, steps, features, or advantages provided in an embodiment where the stimulation and sensing electrodes are within the same pad may also be applied or combined to an embodiment with separate stimulation and sensing pads.

Figure 5:
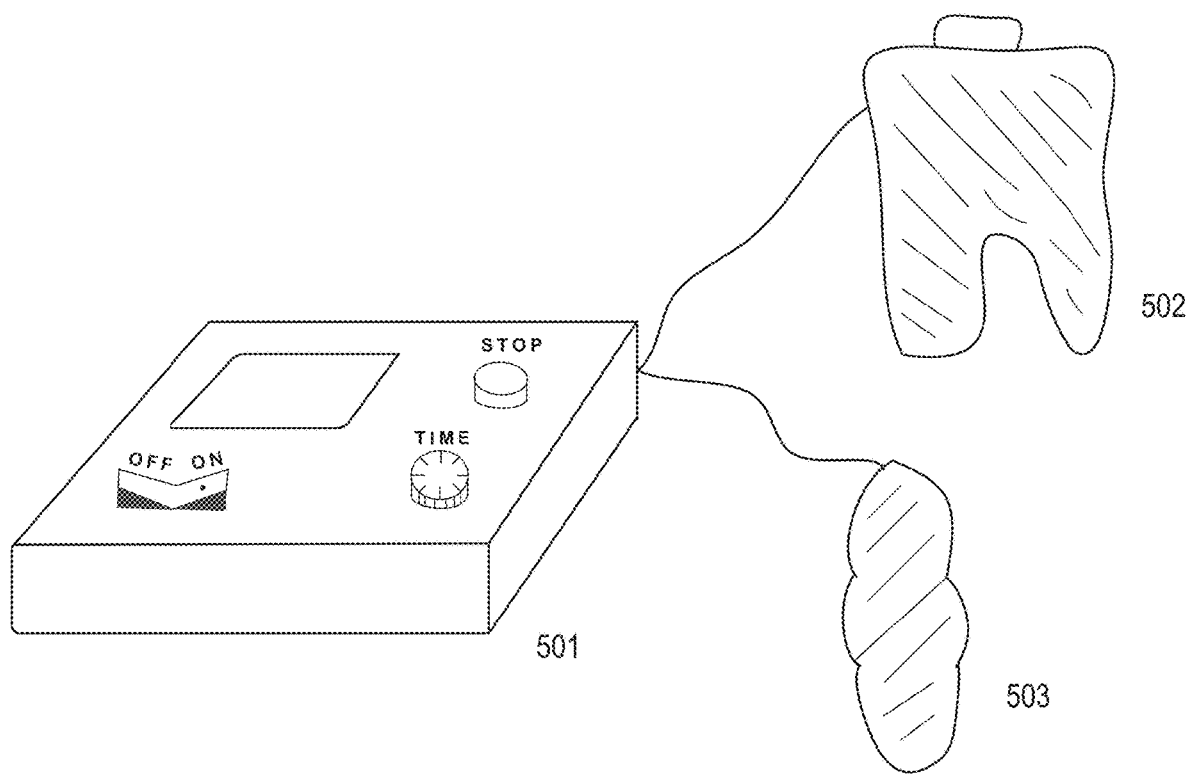
FIG. 5 illustrates an overview of a preferable embodiment of an NMES system with main components.

FIG. 5 shows the major components of a preferable embodiment of the system. An NMES system may include a control unit 501, a stimulation pad 502, and a sensing pad 503. Thus, in some embodiments, a separate stimulation pad and sensing pad may be provided. Any discussion of the system, device, or method relating to a system with a single integrated stimulation pad comprising both stimulation electrodes and sensors may also apply to a system with separate stimulation and sensing pads, and vice versa. Furthermore, in alternate embodiments of the invention, any number of stimulation and sensing pads may be provided within an NMES system, and any discussion herein may also apply to such embodiments.

The NMES system may include a control unit 501, which may include a display and limited operator controls. Some examples of operator controls may include an on/off button or switch, a stop button, or a time knob. Any other device interface mechanisms, including buttons, switches, knobs, touchscreens, light sensors, microphones, speakers, voice-recognition devices, or any other mechanisms known in the art may be utilized to enable an operator to interact with the control unit.

The control unit may also include components such as a signal generator, memory, processor, and power supply. The primary operation of the control unit may be provided by a microprocessor, field programmable gate array (FPGA), application specific integrated circuit, or other suitable mechanism. When activated, the control unit may generate electrical stimulation signals that may be transmitted to the stimulation pad, which couple the energy into the body to activate muscles. Some electrical stimulation parameters, including the duration of therapy, are adjustable by the operator through buttons, knobs, dials, or switches on the control unit. Other electrical stimulation parameters may be optimized through automatic algorithms implemented by the control unit, as outlined below.

An operator may interact with the control unit to initiate the performance of an NMES therapy. For example, in some embodiments, an operator may simply turn the control unit on, and not need to interfere any further throughout the course of the therapy.

In some embodiments, controls may be provided which may enable an operator to intervene during an NMES therapy. For example, a control unit may alert an operator to an alarm condition, which may cause an operator to adjust a parameter, or terminate the therapy. In other examples, the control unit may automatically adjust the parameter or terminate the therapy. In some instances, an operator may adjust a parameter (e.g., the duration of therapy).

The control unit may also enable an operator to enter subject-specific information. For example, an operator may enter personal information about the subject, which may be linked to data generated and/or stored during NMES therapy. In some instances, the information about the subject may affect a therapy parameter.

The NMES system may also include at least one stimulation pad 502. The stimulation pad may include one, two, three, four, or more stimulation electrodes. The stimulation pad may include a plurality of stimulation electrodes and no sensors. Alternatively, the stimulation pad may include both stimulation electrodes and at least one sensor. In some instances, a stimulation electrode may act as a sensor when inactive for delivering electrical stimulation.

The NMES system may include at least one sensing pad 503. The sensing pad may include one, two, or more sensors. The sensors may include sensing electrodes. The sensing pad may include a plurality of sensors and no stimulation electrodes. Alternatively, the sensing pad may include both sensors and at least one stimulation electrode.

In a preferable embodiment, the stimulation and sensing pads may each comprised of a thin and flexible housing with an adhesive backing to facilitate maintenance of skin contact with a person receiving NMES. The backing may also contain hydrogel or other coupling agents to enhance the coupling of electrical energy and signals between sensing or stimulating electrodes and the person's body. The adhesive and/or coupling gels may be located along the entirety of the skin contact side of the pads, or may be located solely in discrete locations (such as underneath electrodes).

The stimulation pad 502 and the sensing pad 503 may be arranged on the subject in any desired manner. For example, the stimulation and sensing pads may be placed on a subject such that the stimulation and sensing pads are not in contact with one another. The stimulation and sensing pads could also be placed on a subject so that there is some overlap of the pads. Preferably, the stimulation and sensing pads will not be mechanically connected to one another, although in some embodiments, they may somehow be interconnected. See, e.g., U.S. Pat. No. 5,549,656, which is hereby incorporated by reference in its entirety.

Furthermore, the stimulation and sensing pads may be separately electrically connected to the control unit, or may share electrical connections to the control unit. In some embodiments, the stimulation and sensing pads may be electrically connected to the control unit via wires. Alternatively, they may be connected wirelessly, or may comprise one or more integrated control unit.

Figure 6:
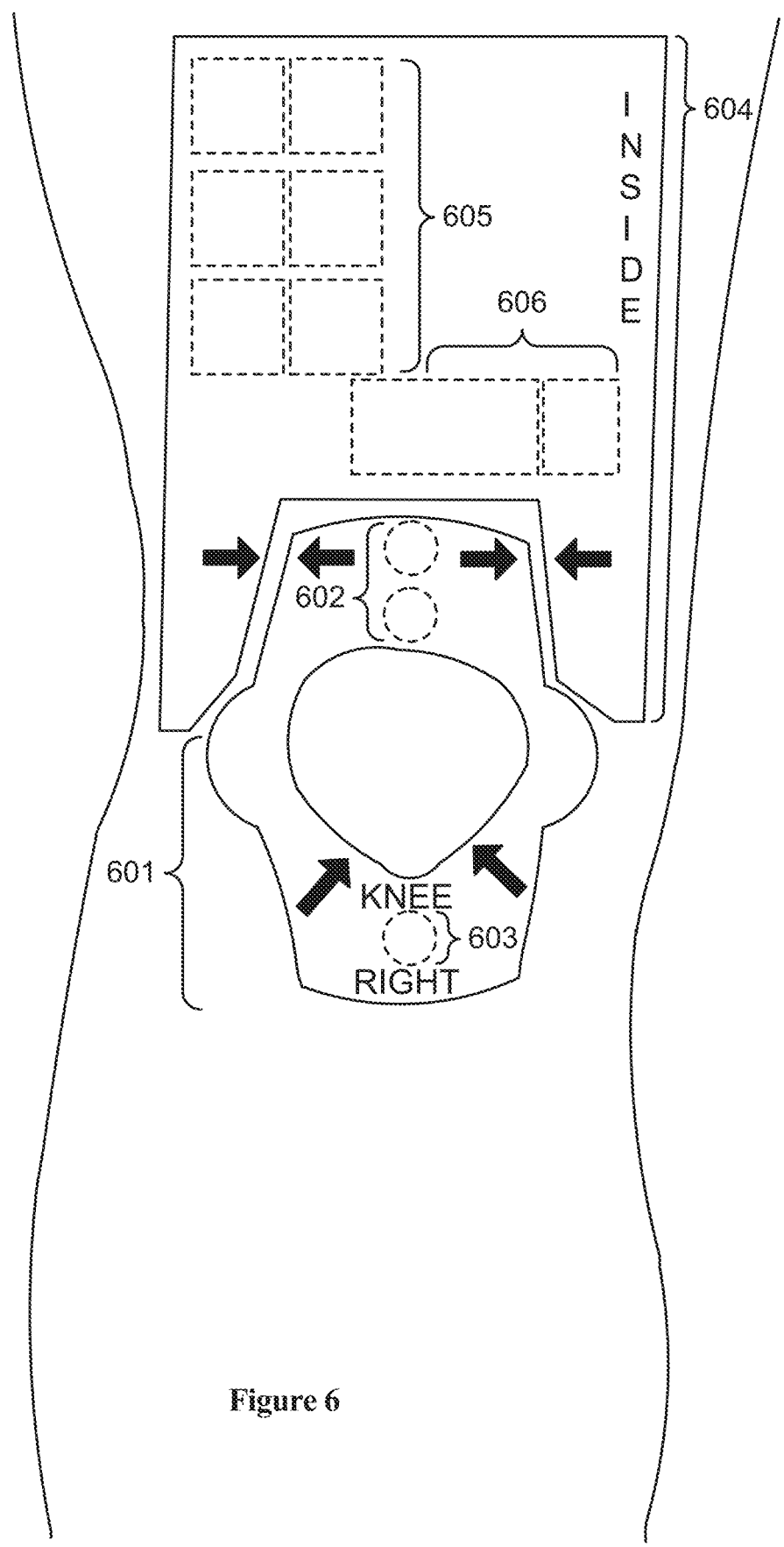
FIG. 6 shows a preferable embodiment of a stimulation pad that may enable efficient use of the method.

FIG. 6 shows a geometry of a preferable embodiment of the sensing pad 601, stimulation pad 604, and the layout of the array of stimulation electrodes in the stimulation pad. The sensing pad 601 may include sensing electrodes used for recording electrical activity 602, and a sensing electrode serving as a ground electrode 603. The stimulation pad 604 may include upper stimulation electrodes 605 in a stimulation electrode array, and lower stimulation electrodes 606 in the stimulation electrode array.

The stimulation pad may contains an array of strategically-placed stimulation electrodes that may be used to deliver electrical energy to muscles and/or nerves in order to produce muscle contraction. The array may be configurable such that, at any given time, only a subset of the electrodes in the array are actively delivering energy to a person receiving NMES. However, electrodes inactive for energy delivery may still be configured to deliver relevant information (such as the electrical impedance between it and a second electrode in the array) to the control unit. The sensing pad may contain one or more sensing element(s) that can detect and record biological parameters that describe muscle contraction directly or indirectly. These sensing parameters may include measurement of direct or indirect electrophysiological features of the muscle contraction or measurements of the mechanical features of the muscle contraction (such as contraction distance, velocity, and acceleration) measured with an accelerometer, a pressure sensitive element, or similar equipment. In a preferable embodiment, electrical signals that are indicative of the state of tension in a tendon are measured by sensing electrodes in the sensing pad.

In a preferable embodiment, sensing electrodes, integrated into a sensing pad, may be placed on the surface of the skin in the region of a tendon that is mechanically coupled to muscles that are stimulated. In some embodiments, the underlying muscle group may be in electrical contact with the stimulation electrodes. The underlying muscle group may be encompassed within a muscle-tendon region. For example, if quadriceps muscles are stimulated to contract, one suitable location for the sensing electrodes would be on the surface of the skin in the region directly over the quadriceps tendon. Tendons are bands of tough fibrous tissue that are composed mostly of collagen fibers, and do not produce electrical activity during muscle contraction in the same way that muscle tissues do. As a result, the majority of electrical activity detected by sensing electrodes located over the tendons arises originally from nearby muscles or from the energy source used to stimulate muscle contraction. Accordingly, these electrical signals travel along and/or around the tendon before reaching the skin surface, where they are detected by sensing electrodes.

In some implementations, one or more sensors may be placed over the tendons to form a linear arrangement along a tendon. For example, if a tendon has a vertical alignment, sensors may be placed over the tendon in a corresponding vertical alignment. The sensors may be placed over or near a tendon such that they are arranged to align in the same direction as the propagation of a signal from a stimulation electrode along the tendon. A sensing pad may include sensors that are configured to be positioned over a tendon along a direction that matches the direction a signal would travel along the tendon.

In some embodiments, the sensors placed on a sensing pad may be outside an area defined by the stimulation electrodes. For instance, sensors may be placed so that they are not between stimulation electrodes.

Without wishing to be bound by any theory, it is believed that the geometry, mechanical properties, and/or other characteristics of the tendon influence its electrical properties (for example, transmission speed and impedance—see Suganuma et al, J Ortho Science 9: 302-309, 2004, incorporated herein by reference). Thus, changes in the state of the tendon may affect electrical signals transmitted to the sensing electrodes. Tendons connect muscles to bones, and transmit forces that arise due to muscle contraction. Accordingly, tendons are capable of withstanding tension during muscle contraction. Without wishing to be bound by any theory, it is believed that a stronger muscle contraction produces more tension and a greater geometry change in an associated tendon and adjacent anatomical regions than a weaker muscle contraction. It would follow that a stronger muscle contraction would alter both the electrical properties of the tendon and the available electrical transmission pathways, and thus the electrical activity detected by the sensing electrodes located over or beyond the tendon, more than a weaker muscle contraction. Specifically, it is believed (as proposed by Suganuma et al) that increased tendon tension leads to increases in tendon electrical impedance. Thus, electrical activity detected over or near tendons is suitable for optimization of techniques, including electrical stimulation, that produce muscle contraction and induce changes in tendon geometry and tension.

Sensing electrodes placed over tendons and novel signal processing algorithms developed to expose the effects of tendon properties and geometry on recorded signals offer many advantages over traditional NMES optimization methods. Standard electromyography (EMG), defined here as measuring the electrical activity produced by muscle contraction using surface or needle electrodes placed in the region of contracting muscles, has limited usefulness during electrical stimulation due to interference between electrical signals injected into the body by the stimulator (on the order of 10-50 V) and electrical signals produced by muscles (on the order of 5-50 mV). Current clinical and engineering research has focused upon the development of complex, often adaptive, signal filters to extract useful information from EMG data collected during electrical stimulation. However, problems with extracting useful EMG data during electrical stimulation are exacerbated when an array of stimulation electrodes are used, because the interference pattern between the stimulation energy artifact and the muscle activity data will not be constant among all data acquisitions, leaving previously developed EMG filters generally not applicable or of limited utility. As described in detail below, signal processing algorithms that extract information concerning tendon tension and geometry from electrical signals recorded over tendons do not suffer from performance degradations or interpretation uncertainty due to electrical stimulation/EMG signal interference.

When muscle stimulation is applied to critically ill patients, further advantages of optimization methods based upon tendon tension and/or geometry are evident. In the ICU and many other environments, the use of needle electrodes to measure EMG data is generally not suitable, and surface electrodes must be used. Critically ill patients often suffer from tissue edema (swelling) as a side effect of treatment. It is believed that the presence of significant edema will generally result in a greater distance between muscle tissues and the skin, attenuating and distorting EMG data that are collected with electrodes on the skin surface. In many cases, no useful EMG data can be acquired. Similar problems exist when using surface electrodes to measure EMG data from obese persons or persons with low baseline muscle mass. Deposits of fatty tissue and tissue edema are typically at local minima around bony prominences, such as the knee, where tendons insert. Thus, electrical activity measured over the tendon (or, as shown below, even over the bony prominence itself) may produce data more reliable than EMG data in these persons. Signal processing algorithms developed to interpret these data may thus enable indirect measurement of muscle contraction when useful EMG data are unobtainable. Additionally, critically ill patients are most often treated while lying in bed with legs extended. As legs are already extended, the stimulation of the quadriceps produces little physical movement, limiting the utility of sensors such as accelerometers that seek to optimize the electrical stimulation location or parameters based upon measurements of muscle dynamics.

It should be noted that in order to implement a preferable embodiment of the method, it is not required that sensing electrodes be placed directly over the tendon with a high degree of precision. It is only required that the sensing electrodes be close enough to the target tendon such that the varying electrical properties, geometry, and other properties of the tendon during muscle contraction significantly impact the electrical activity waveform detected by the sensing electrodes. As described below, by using sensor pad geometries tailored to the local anatomy in the region of stimulation, it is possible to ensure that sensing electrodes are placed close enough to the target tendon in order to empower the successful implementation of the method.

As shown in FIG. 6, a preferable embodiment will utilize stimulation and sensing pads with a specific overall geometry, or footprint. The stimulation and sensing pads shown in FIG. 6 may be tailored for the stimulation of quadriceps muscles, although those skilled in the art will recognize that similar principles can be applied to design pad geometries tailored to the stimulation of other muscle groups. The geometry of the sensing pad may be designed such that the sensing electrodes will make contact with a person's skin superior to the knee, in the region of the quadriceps tendon.

The unique shape of the sensing pad 601 may use a readily identifiable anatomical marker (e.g., the knee cap) both to ensure proper placement of the sensing electrodes over the quadriceps tendon and to ensure proper alignment with the stimulation pad (as elaborated upon below). The sensing pad may include a protruding feature to match the protrusion provided by the knee cap to create a desirable alignment of the sensing pad. In some instances, the anatomical feature provided on the sensing pad may be a hole that may enable the knee cap to protrude through the hole. Other examples of anatomical features may include a different material over the knee cap region, that may enable the knee cap to more easily stretch the sensing pad at the knee cap, or some sort of visual indicator, such as a color change or line that may indicate the placement of the knee cap. Thus, the sensing pad may include an anatomical placement guide that may assist with placing the sensors at a desired location.

The sensing pad 601 may utilize three sensing electrodes: two electrodes 602 intended to collect electrical signals to be used as inputs to a differential amplifier and/or other signal conditioning circuitry, and a reference electrode 603 placed over a bony prominence some distance from the other electrodes (for example, the shin near tibia). Alternatively, as few as one sensing electrode may be utilized to extract sufficient information required to optimize electrical stimulation parameters. Similarly, at least one signal collecting electrode and at least one ground electrode may be provided. Variations of a preferable embodiment of the system can utilize more than three sensing electrodes to extract information concerning tendon tension and/or geometry. In these variant embodiments, information from individual sensing electrodes may be analyzed individually, and may or may not be compared with the use of a differential amplifier or similar hardware or software.

In some embodiments, the signal collecting electrodes 602 may be placed on the sensing pad so that they are at the lower thigh above the knee cap. In some instances, they may be vertically directly above the knee cap, while in other embodiments, they may be horizontally spaced. Preferably, the signal collecting electrodes may be arranged some distance from the reference electrode 603 (aka ground electrode).

The reference electrode may be spaced apart from the other signal collecting electrodes. In some embodiments, a reference electrode may receive very little or no electrical signals that are provided from the stimulation electrodes. A reference electrode may pick up inherent background electrical signals from the subject body. In some instances, the signals collected by the other signal collecting electrodes may be compared to the signals provided by the reference electrode to compare which signals are provided by the stimulation electrodes and muscle properties as compared to background signals. In some instances, the background signals provided by the reference electrode may be subtracted from the signals collected by the other signal collecting electrodes.

The top portion of the sensing pad may be shaped to have a protrusion that fits into a notch-shaped opening in the stimulation pad 604. Any shape that may allow the sensing pad to align with the stimulation pad may be provided. For example, the sensing pad and the stimulation pad may have complementary shapes, so that an extension from one pad may have a corresponding indentation in the other pad. This geometry may allow for the usefulness of the knee cap as an anatomical marker to be extended to aid in accurate gross positioning of the stimulation electrode array. This geometry may increase both intra- and inter-operator consistency of stimulation pad placement by creating a virtual anatomical reference point (the protrusion of the sensing pad) in a region of the body (the thigh) that lacks readily identifiable anatomical markers. Additionally, this geometry may be designed specifically to fix the position of the stimulation electrodes with regard to the sensing electrodes, and to minimize deviations from the ideal spatial relationship between the two sets of electrodes. In some embodiments, additional visual indicators or markers, such as arrows on the sensing and stimulation pads, may provide additional aids in aligning the sensing and stimulation pads. Thus, visual markers may aid in fixing the spatial relationship of the sensing and stimulation pads.

The stimulation pad 604 may contain an array of stimulation electrode contacts, each of which can be individually enabled or disabled automatically by the control unit to provide energy to the person receiving NMES. The use of an array of electrode contacts enables the gross placement of the stimulation pad on a person in the desired region of stimulation, without requiring precise alignment of individual electrode contacts over the motor points of the muscle. A preferable embodiment of the stimulation pad may comprise an array of eight square or rectangular stimulation electrode contacts arranged in a particular pattern. It will be clear to those skilled in the art that other arrangements of the stimulation electrode array and other electrode contact shapes and sizes could be employed without loss of generality. Similarly, a different number of individual stimulation electrode contacts in the array could be employed to empower the use of the disclosed method, such as one, two, three, four, six, nine, ten, twelve, fifteen, twenty, or more stimulation electrode contacts. The stimulation electrode contacts may be placed at any location of the stimulation pad. Stimulation pads designed to be used with muscle groups other than the quadriceps will likely contain stimulation electrode arrays with markedly different arrangements.

The particular arrangement of the stimulation electrode array portrayed in FIG. 6 can be used to enhance the performance of an automatically optimizing electrical stimulation system. Stimulation electrodes comprising the array can be classified as being part of one of two groups: upper electrode contacts located near the bulky part of the thigh 605, or lower electrode contacts located closer to the quadriceps tendon 606. During NMES therapy, most commonly the energy delivered by the system will travel between one or more upper electrode contacts and one or more lower electrode contacts. Upper electrode contacts may be positioned to make contact with the middle-outside of a person's thigh (expected location of a motor point), and span a length (for example, six inches) expected to be larger than the span of possible motor point locations in an average adult. Lower electrodes may also positioned close to the location of an expected muscle motor point, and are also positioned in a manner so as to dictate the direction of current flow through the leg. In some embodiments, the larger lower electrode need not be centered along the midline of the thigh. Instead, it may be arranged so that its center point is slightly toward the inside of the thigh, causing energy traveling between upper and lower electrode contacts to cross the midline of the thigh. An additional, smaller lower electrode may be positioned at a similar distance superior to the knee cap, but more to the inside of the leg. The electrode contact placement may depend on the target muscular stimulation.

In accordance with an embodiment of the invention, an NMES system may be provided, wherein the NMES system comprises a stimulation assembly. The stimulation assembly may be formed with a plurality of electrodes and at least one sensor, where the sensor may be positioned within a predefined range away from each electrode to monitor the remote effects of electrical stimulation from the electrodes on a selected muscle-tendon region of the body. The predefined range may depend on the target muscle-tendon region of the body. For example, one or more sensing electrode may be placed near a bony prominence near an underlying tendon. The stimulation electrodes may be at a range of distances from the sensing electrodes. In one example, if the target muscle-tendon region is the quadriceps, the sensing electrodes may be place near a knee, such as above the knee, and the stimulation electrodes may be placed over the quadriceps, since range of distance d from the sensing electrodes.

The NMES system may also include a control unit connected to the plurality of electrodes, and the sensor. The control unit may provide stimulation signals to the electrodes and receive a signal from the sensor. In some instances, the stimulation signals provided to the electrodes may depend on the signals received by the sensor.

Figure 7:
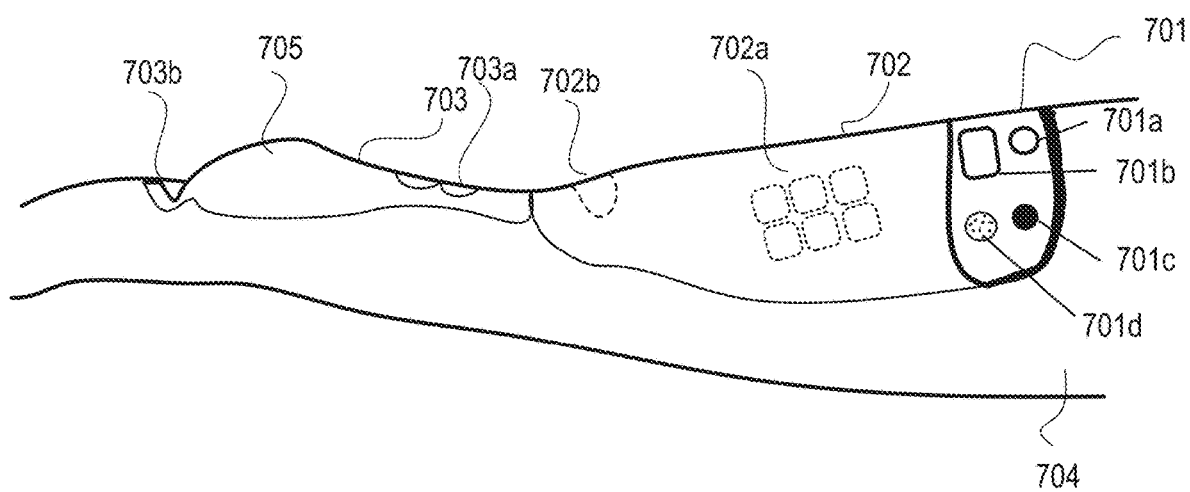
FIG. 7 illustrates an alternative embodiment of an NMES system with a control unit integrated into a stimulation pad.

FIG. 7 illustrates a side view of an NMES system where a control unit 701 may be integrated into a stimulation pad 702. The system may also include a sensing pad 703, which may or may not be integrated together with the stimulation pad. The stimulation and sensing pads may be placed on a leg 704 of a subject.

The control unit 701 may include a display and any operator interface devices 701*a*, 701*b*, 701*c*, 701*d* that may enable an operator to interact with the control unit.

The stimulation pad may include an array of stimulating electrodes, which may be arranged in any matter on the stimulation pad. For example, the stimulating electrodes may be grouped into upper electrodes 702*a* and lower electrodes 702*b*. The control unit may determine electrical stimulation parameters for signals provided to the stimulation electrodes.

The sensing pad may include one or more signal collector electrodes 703*a*, and one or more ground electrode 703*b*. The ground electrode may be located over a bony prominence, such as over a shin. In some embodiments, the ground electrode may be located below a knee, while the signal collector electrode may be located above the knee.

The sensing pad and/or stimulation pad may be able to accommodate underlying anatomical features. For example, when the pads are placed on the front of a leg 704, the sensing pad may be shaped with a protrusion to accommodate the protrusion provided by a knee cap 705.

The NMES system may be applicable to other anatomical regions as well. Such systems may make use of other anatomical features, such as protrusions, anatomical shaped regions, bony prominences, and so forth. For example, the NMES system may target muscle tissue provided in the calves. The stimulation and/or sensing pad may utilize a bony prominence, such as a knee or ankles as an anatomical marker, and may have an anatomical placement guide that conforms to the shapes of the anatomical markers.

In another example, the NMES system may target muscle tissue in the upper or lower arms, and may utilize anatomical features to place the stimulation and/or sensing pads. For example, the pads may be shaped to fit over bony prominences such as elbows or wrists, or may use other anatomical features as guides, such as armpits.

The NMES system may also target muscle tissue in the torso of a subject. For example, the system may provide stimulation to a subject's waist, and may use the subject's hip as an anatomical guide, or may provide stimulation to the subject's upper torso, and may use anatomical features such as armpits as a guide. The NMES system may target any other muscle tissue in a subject's body and may include a stimulation and/or sensing pad with an anatomical placement guide that may guide the pad to a desired location.

Figure 8:
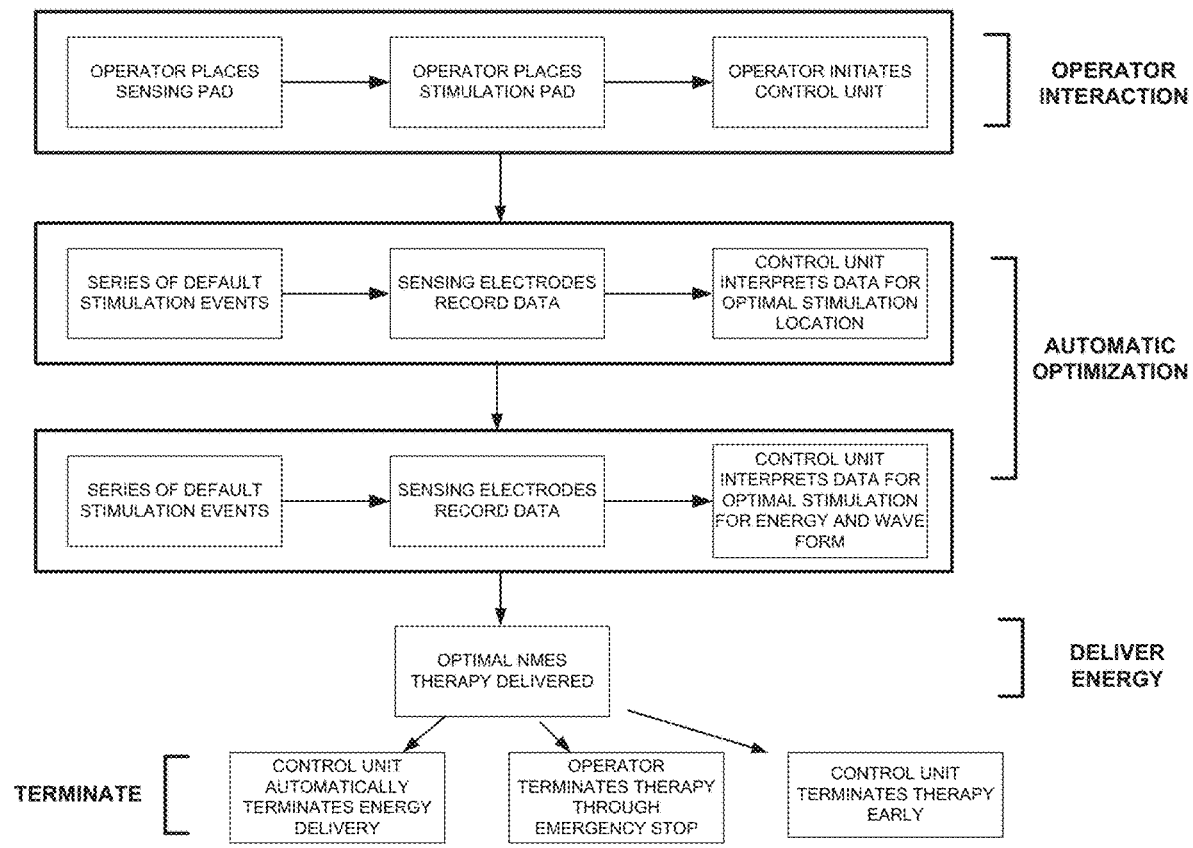
FIG. 8 is flow chart illustrating a number of the major steps in a preferable embodiment of an NMES method.

FIG. 8 is a flow chart outlining the major steps in a preferable embodiment of an NMES method. For example, the major steps may include operator interaction, automatic optimization, energy delivery, and termination. Each of the major steps may include minor steps. Any of the steps described may be optional, interchangeable with another step, or may occur in a different order than described.

For example, operator interaction may include (1) an operator placing a sensing pad on a subject, (2) an operator placing a stimulation pad on a subject, and (3) an operator initiating a control unit. Automatic optimization may include (1) running a series of default stimulation events, (2) having sensing electrodes record data from the default stimulation events, and (3) a control unit interpreting the sensing electrode data for an optimal stimulation location. In some instances, this may be provided as a calibration sequence. Automatic optimization may also include (4) providing a series of default stimulation events, (5) having sensing electrodes record data from the stimulation events, and (6) interpreting data for optimal stimulation for energy and waveform. This may occur repeatedly and/or continuously throughout the NMES method. An energy delivery step may include delivering an optimal NMES therapy. The signal to be provided by the stimulation electrodes may be determined by a control unit during automatic optimization. Termination may occur when a control unit automatically terminates energy delivery, when an operator terminates therapy through an emergency stop, or when the control unit terminates therapy early. The steps may be discussed in greater detail below.

A preferable embodiment of the method of delivering NMES may begin with an operator placing the stimulation and sensing pads on the person receiving therapy. Once the pads are in place, the operator may initiate therapy by pressing a button, flipping a switch, connecting two components, or another suitable action. Following this action, no other operator actions are required to optimize and deliver NMES to the person. After the control unit is initiated, a preset algorithm may sequentially deliver stimulation energy waveforms of known shape, duration, and amplitude to pairs or groups of stimulation electrodes in the array. Although a great number of stimulation waveforms could be used for this preset calibration step, example waveforms could be characterized by a 5 second train of asymmetric, biphasic square wave pulses of 300 µs duration and 50 mA average peak electrical current repeating at a rate of 40 Hz, with the train having amplitude ramp-up and ramp-down periods of 1 second (i.e., 3 seconds of full amplitude energy delivery). Sensing electrodes in the sensing pad may simultaneously record the electrical activity measured over the tendon during each stimulation event. This electrical activity may represent some combination of the stimulation energy directed into the body by the device and the underlying muscle electrical activity (i.e. M-waves) resulting from contraction. Information detected by the sensing electrodes may be transmitted to the control unit, where it may be filtered and stored into memory. Alternatively, electronics for filtering of electrical activity waveforms may be located on the sensing pad itself. Filtering steps may include high and/or low pass filters as well as adaptive and/or non-linear signal processing to remove electrical activity produced by the stimulation electrodes and other electrical noise generated by the surrounding environment.

Following the execution of a default series of stimulation events and the storing of the electrical activity associated with each event in memory, software and/or hardware mechanisms located in the control unit or on either the sensing or stimulation pad may be used to compare the various electrical activity waveforms recorded by the sensing electrodes. For example, signals from the sub-threshold or low amplitude stimulation may be compared to those of super-threshold or high level stimulation. The goal of the comparison may be to search for the pair or group of stimulation electrodes in the stimulation array that produced the strongest and/or most efficient muscle contraction. Electrode placement may be optimized or improved using such techniques.

In a preferable embodiment, electronics such as a microprocessor, FPGA, or other suitable means located in the control unit will execute algorithms intended to measure the total energy in the sensed electrical waveforms, the relative energy drop detected between pairs of sensing electrodes, the energy located in certain portions of the electrical waveforms, or the slope of waveform energy change vs. the amplitude of energy delivered to the body by the stimulation electrodes. Those skilled in the art will recognize that alternative embodiments of the described method could use other types of waveform evaluations and signal processing steps to achieve similar endpoints.

Experience has shown that the shape or type of the electrical activity waveforms measured over the quadriceps tendon will vary based upon the placement of the active (i.e., used to deliver and/or receive energy) lower electrode(s) relative to the tendon. It is believed that the shape or type of the electrical activity waveform is a function of the muscles stimulated by a given pair or group of electrodes, the state of the tendon induced by the muscle contraction, the electrical path between stimulation electrodes, sensing electrodes, and other local anatomy, and potentially other factors. It is thus believed that similar phenomena may alter the shape of electrical activity waveforms sensed around tendons in other anatomical regions, as well. Knowledge of the shape or type of the waveform may in some instances be vital for successful implementation of a preferable embodiment of the disclosed method. Specifically, it may be important and preferable that each potentially used pair or group of stimulation electrodes produces the same shape or type of electrical activity waveform, as measured by sensing electrodes placed on or nearby the tendon. While waveforms of similar shape or type can be compared accurately with signal processing algorithms to search for subtle differences resulting from differing electrical properties of the tendon, comparison of waveforms with markedly dissimilar shapes will generally miss these subtle differences.

FIGS. 9(a) and 9(b) illustrate example electrical activity waveforms measured by sensing electrodes placed over a quadriceps tendon. Although each waveform may be a single electrical trace, portions of interest (what may be defined as the response pulses) in the waveforms have been highlighted in bold for illustrative purposes. The electrical activity waveforms may include examples of the large stimulation pulses 901, examples of monophasic response pulses 902, and examples of biphasic response pulses 903. Lower electrodes may be positioned to produce the electrical activity waveforms. A major factor in the determination of waveform shape may be the location of the lower stimulation electrode(s) with respect to the quadriceps tendon.

FIGS. 9(a) and 9(b) show examples of two different electrical activity waveform shapes resulting from stimulation of the quadriceps muscle. Waveforms were recorded with sensing electrodes arranged and placed as shown in FIG. 6 and with the two superior located electrodes 602 serving as inputs to a differential amplifier circuit. These examples are provided for illustrative purposes, and those skilled in the art will recognize that other waveform shapes are probable in different anatomical locations and that different stimulation electrode array configurations and sensing electrode locations will produce variations of the depicted waveform shapes as detected over the quadriceps tendon. Depicted in FIG. 9(a) is a subset (zoom-in) of the electrical activity sensed when the smaller lower electrode is disabled and the center of the larger lower electrode may be located slightly to the outside side of the quadriceps tendon. Depicted in FIG. 9(b) is a subset (zoom-in) of the electrical activity sensed when the smaller lower electrode is disabled and the center of the larger lower electrode may be located slightly to the inside side of the quadriceps tendon.

Figure 9:
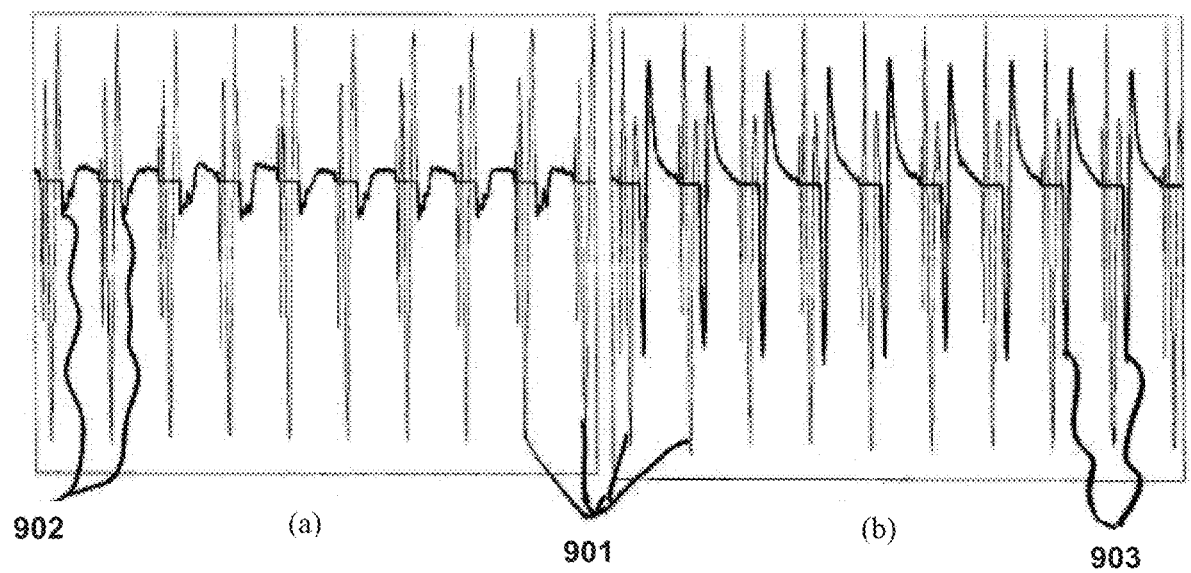
FIG. 9 shows examples of electrical activity response waveform shapes, with corresponding electrical stimulation locations to produce said waveform shapes.

Both of the electrical activity waveform shapes shown in FIG. 9 are comprised of two sets of pulses that repeat at the rate of stimulation (in this case, 40 Hz). The larger amplitude pulses (for example, 901) may be related to the NMES energy supplied to the person by the control unit/stimulation electrodes. The smaller pulses (for example, 902 and 903) may result from the electrical activity produced by muscle contraction (i.e. EMG M-waves), any residual effects of the stimulation energy supplied to the body, and potentially other sources. These smaller pulses may also be referred to as response pulses. The shape of these response pulses may be important to enable effective comparison using a preferable embodiment of the method. In this disclosure, the shape of the response indicated by 902 may be monophasic and the shape of the response indicated by 903 may be biphasic.

In a preferable embodiment of the method, it is desirable to use sensed electrical activity waveforms with biphasic response pulse shapes. The biphasic waveform response may optimize the tradeoff between the predictive power (with regard to ideal muscle stimulation location and strength) of the electrical activity detected by the sensing electrodes and the quality of the muscle contraction induced in the quadriceps muscle. Without wishing to be bound by any theory, it is further believed that biphasic nature of the response pulse arises when conditions allow for a portion of the original electrical activity waveform to interfere with other electrical activity measured by the sensing electrodes. This interfering electrical activity could originate from M-wave or stimulus pulse reflections from the tendon or surrounding anatomy, H-reflex interference, or from other sources.

Given the stimulation pad and sensing pad geometries shown in FIG. 6, most NMES operators will place the stimulation pad in a way such that the muscle stimulation induced by sending energy between any upper electrode in the array and only the larger lower electrode will produce an electrical activity waveform detected by the sensing electrodes that has a biphasic shape. In a preferable embodiment, software algorithms may verify proper placement of the stimulation pad by ensuring that the electrical activity waveform recorded by sensing electrodes contains biphasic response pulses. For example, this could be done by comparing the maximum positive and negative amplitudes of the response pulses (not of the larger stimulation pulses indicated by 901). If the response pulses were determined to not be suitably biphasic, the smaller lower stimulation electrode may be activated such that stimulation energy travels between one or more upper stimulation electrodes and both lower stimulation electrodes in tandem. This effectively shifts the lower stimulation energy location more to the inside of the leg, making the response pulses detected by the sensing electrodes more biphasic, and thus more useful.

Following the initial series of preset stimulation events, the storage of electrical activity waveforms in memory, and confirmation that the electrical activity waveforms produced by each pair or group of stimulation electrodes all contain similar shaped response pulses (ex. biphasic, monophasic, or another shape not explicitly illustrated in this disclosure), signal processing algorithms will compare the electrical activity waveforms to determine which pair or group of stimulation electrodes may be ideal for use (closest to muscle motor points) during NMES therapy. These comparisons may be performed by assessing the electrical waveforms for indications of tendon tension. Stronger muscle contraction may lead to more tendon tension, leading to both increases in the electrical impedance of the tendon and geometry changes in the tendon and surrounding anatomy. It is believed that these tendon changes may further lead to an increased amplitude of electrical activity being measured at the tendon. This increase in energy may be due to increased reflection of energy at or near the tendon. Similar to physics governing transmission line theory, as electrical waveforms encounter resistive loads, a portion of the waveform is absorbed by the load (in this case, tendon) and a portion is reflected. Waveform reflections may also arise due to changes in geometry of the tendon or surrounding anatomical structures that may change geometry in response to increased tension in the tendon. It is also possible that energy increases may arise from other sources, such as H-reflex interference or other factors. Signal processing mechanisms may be utilized to extract the energy contained in response pulses as an indirect but accurate measure of muscle contraction strength. This method may offer significant advantages over EMG and other measures of muscle contraction strength in critically ill and other groups of persons, and can thus enable more accurate and reliable optimization of NMES.

Thus, in some embodiments, a sensor located over or near a tendon may measure large amplitude pulses (e.g., comparable to 901) from a stimulation electrode. In some embodiments, a tendon sensor may measure relatively little or no EMG signals. In some instances, no further amplification of the signal received from the sensor may be necessary. Thus, preferably, the signal received by a tendon sensor (located over or near a tendon) may be unamplified. For instance, no differential amplifier may be used to increase smaller pulses (e.g., pulses comparable to 902 and 903). In alternate embodiments, some amplification may occur. Thus, as previously mentioned, the use of a tendon sensor may offer an advantage over traditional EMG by not requiring additional amplification components.

In a preferable embodiment of the system shown in FIG. 6, the (non-ground) sensing electrodes 602 may be configured to each serve as an input to a two-channel differential amplifier. In this configuration, the sensing electrodes may be used to collect data that are indicative of reflection and other tendon-induced changes in the response pulse shape, amplitude, and other characteristics. In this configuration, the stimulation electrode pair or group that produces the strongest muscle contraction may produce response pulses that contain the most energy. The major differentiator in the energy contained in the response pulses may be related to the amount of tension in the tendon. In a preferable embodiment, signal processing methods may extract the total energy contained in the response pulses by: i) filtering out or removing larger stimulation pulses (e.g., those of type indicated by 901) from the recorded electrical activity waveform, ii) taking the absolute value or the envelope of the remaining waveform, iii) integrating or tallying a cumulative sum of remaining waveform data to estimate the total energy of the response pulses contained in the waveform. Step iii) allows for small amplitude differences that occur repeatedly over many stimulation events to produce more robust (i.e. higher contrast) energy estimates. Alternative signal processing methods could only apply steps ii) and iii) without filtering out or removing the larger stimulation pulses from the recorded electrical activity waveform. An alternative embodiment of the method could involve a more extensive series of preset stimulation events, with the default stimulation train applied to each potential pair or group of stimulation electrodes being repeated with two or more average electrical current amplitude levels. In this scenario, signal processing algorithms could implement steps i)-iii) as outlined above, but may also add a fourth step that may determine how the energy contained in the electrical activity waveform changes with changes in the applied stimulation energy. Without wishing to be bound by any theory, it is believed that the pair or group of stimulation electrodes that produces the largest change in sensed electrical activity energy with increasing applied stimulation energy will be the most suitable for providing effective NMES therapy. In further embodiments of the method, analysis could involve the use of amplitude threshold detectors, integrator circuits or algorithms, comparator circuits or algorithms, or other similar techniques.

Given the belief that changes in tendon tension and/or geometry may cause changes in the degree of reflection (if any) of the response pulses or other changes (ex. from H-reflex or other sources) in the interference pattern measured by the sensing electrodes, a variation of an embodiment of the system and signal processing described above is possible.

Figure 10:
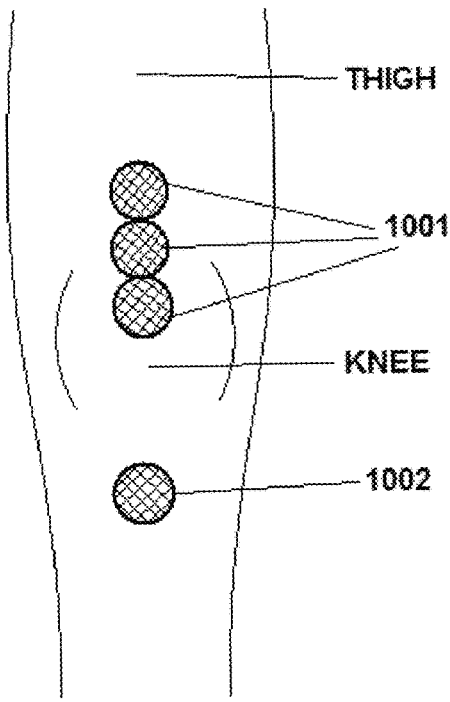
FIG. 10 shows an example functionality of a variation of a preferable embodiment with example electrical activity data demonstrating usefulness and functionality.
Figure 10:
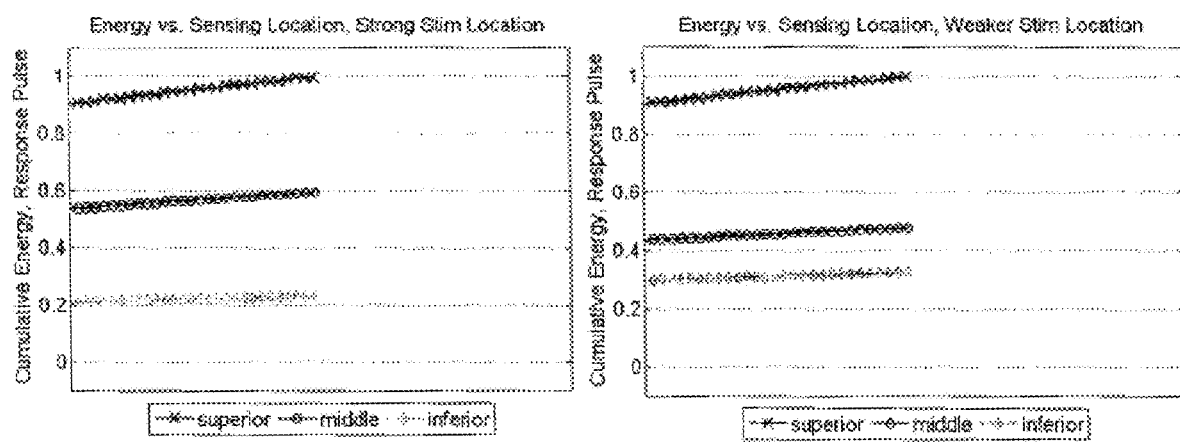

As shown in FIG. 10(a), a different configuration of the sensing electrodes is used in this variation. In this configuration, the three sensing electrodes near the knee 1001, referred to individually as the superior, middle, and inferior electrodes, may be utilized to collect electrical signals for analysis. A fourth sensing electrode 1002 that acts as a reference (or 'ground') may be located over a bony prominence further from the region of stimulation, for example over the shin. Each non-ground electrode may collect waveform voltage data (with reference to the reference electrode) individually. In some configurations, the voltage signals from the superior or middle electrodes may be used as one input to a differential amplifier, with the signal from the inferior electrode serving as the second input to the differential amplifier, with the ground electrode signal serving as circuit ground. In some other configurations, no differential amplifier is used in conjunction with the superior, middle, and inferior electrodes. As previously discussed, any arrangement or number of sensing electrodes may be utilized.

In one implementation, the superior and middle electrodes may be placed at the lower thigh right above the knee. The inferior electrode may be directly on the knee cap. In some instances, tendon may be stretch over the knee cap and the inferior electrode over the knee cap may be in electrical communication with the underlying tendon. The reference electrode may be at the shin directly below the knee. Stimulation electrodes may be positioned on the thigh above the sensing electrodes. The superior and middle electrodes, and the inferior electrodes may be able to measure electrical signals that may be affected by the stimulation electrodes. In some embodiments, the superior, middle, and inferior electrodes may be aligned in a linear fashion. In some embodiments, they may be aligned to correspond to the direction of the underlying tendon. For example, one or more sensors may be aligned over a tendon to correspond to the direction of a signal traveling along the tendon. In some instances, this may provide an alignment that is substantially parallel to a longitudinal axis defined by the length of a straightened leg.

At least one stimulation electrode may be placed at some distance from a sensor. For example, a stimulation electrode may be placed at least 0.5 inches from a sensor. A stimulation electrode may be positioned over muscle and/or nervous tissue, while a sensor electrode may be positioned over a tendon (as opposed to the muscle and/or nervous tissue). Preferably, a sensor may be placed over a tendon corresponding to the muscle tissue stimulated by the stimulation electrode, such that the sensor may receive signals from the corresponding muscle and/or nervous tissue, the electrical pulses used to excite the muscle and/or nervous tissue, or both.

A stimulation electrode may apply stimulation to the underlying muscle and/or nervous tissue, which may cause the muscles to contract. The signal used to excite tissue or cause muscle contraction may travel along the body away from the site of stimulation. This may include measurable signals traveling through or near the tendon. The signals may be measurable by the sensors at the tendon. Changes in tendon tension, geometry, or other properties caused by the contraction of a mechanically connected muscle may alter signals traveling through or near the tendon, and the amount of change may be indicative of the degree of muscle contraction. Such signals may be measurable and useful (e.g. for optimization) at the tendon, even in a raw state (e.g., without amplification). This may provide advantages over traditional EMG systems which were measuring signals that would usually be too weak to be measured at that distance in a raw form (i.e. without amplification or use of a differential amplifier). This may also be advantageous for subjects with weak muscle interactions.

The sensors may be directly adjacent to one another with little or no spacing between them. For example, the sensors may be approximately 0.5 inches in diameter, so that when three sensors are placed next to one another, they take up about 1.5 inches. Alternatively, the sensors may be provided to have some spacing between one another. The sensors may have any dimensions (e.g., diameters of about 0.1 inches, 0.2 inches, 0.3 inches, 0.4 inches, 0.5 inches, 0.6 inches, 0.7 inches, 0.8 inches, 0.9 inches, 1.0 inches), and any number of them may be provided spaced at any distance apart.

The signals measured by the sensors along the length of the tendon may vary in amplitude and/or magnitude in accordance with the distance of the sensor from a stimulation electrode. For example, if a stimulation electrode is placed over a muscle on a thigh, and delivers an electrical stimulation signal, the signal may travel to the corresponding tendon and propagate along the length of the tendon. The sensor over the tendon that is closer to the stimulation electrode may measure the stimulation signal with a greater amplitude than a sensor that is further from the stimulation electrode since the stimulation signal may degrade along the length of the tendon.

In some embodiments, a reference electrode placed below the knee may be able to measure background electrical signals from the subject without measuring (or only minimally measuring) signals from the stimulation electrodes. The reference electrode may be at a sufficient distance from a stimulation electrode so as to substantially not measure a signal from the stimulation electrode. The reference electrode may be placed such that underlying anatomical features or intervening anatomical features may substantially prevent a signal from a stimulation electrode from being measured by the sensor. In some embodiments, the signals from the reference electrodes may be subtracted from the signals measured by the superior, middle, and inferior electrodes, to measure the activity in the sensing electrodes minus the natural electrical background.

In this embodiment, electrical signals measured at each sensing electrode may each first be processed individually using steps i)-iii) described above. Following this, the energy levels in the processed electrical waveform measured at each electrode may be normalized by the strongest energy level (detected from the superior electrode) and compared. The normalization step is a useful because it removes any dependency on overall waveform amplitude, which can be noisy or unreliable, for optimization of NMES. The strongest muscle contraction may induce the most tension and greatest geometry change on the tendon and surrounding anatomy, and thus produce the greatest amount of energy change (due to reflection, interference, and/or other factors) between the middle and inferior electrodes. Therefore, it is hypothesized that stronger contractions will produce response pulses with a relatively larger percentage of the original energy (as detected by the superior electrode) detected at the middle electrode and a relatively lower percentage of the original energy detected at the inferior electrode. Thus, one suitable algorithm to determine the pair or group of stimulation electrodes that produces the strongest muscle contraction would look for the largest difference in energy calculated at the middle and inferior electrodes, respectively. Because only relative energies are compared, for this variation of the system embodiment it may not be vital to ensure that the response pulse shapes (ex. monophasic vs. biphasic) are similar prior to comparison. It is noteworthy that in this variation of the embodiment, the pair or group of stimulation electrodes selected as optimally located need not necessarily be the pair or group that produces the strongest overall energy amplitude as measured at any individual sensing electrode. Those skilled in the art will recognize that many variations of the described signal processing algorithms for this embodiment and others can potentially be used to extract information related to changes in tendon tension and geometry from available data.

FIG. 10(a), shows an embodiment that utilizes a different configuration of the sensing electrodes. Three sensing electrodes around the knee 1001, referred to individually as the superior, middle, and inferior electrodes, may be used to measure electrical activity relative to a ground electrode 1002. As shown in FIGS. 10(b) and 10(c), example plots of the cumulative energy contained in electrical activity response pulses for muscle stimulation that leads to 10(b) a strong contraction and 10(c) a weaker contraction.

FIGS. 10(b) and 10(c) show example functionality and usefulness of an embodiment. The normalized cumulative energy plots (see steps i)-iii) described above) for a series of response pulses are shown for each of the three sensing electrodes for stimulation electrode pairs that may produce strong FIG. 10(b) and weaker FIG. 10(c) muscle contraction (and thus tendon tension). Shown are actual waveforms acquired by applying electrical stimulation to human quadriceps muscle and recording electrical activity data using the sensing electrode configuration shown in FIG. 10(a). In FIG. 10(b), the middle electrode records ~60% of the energy recorded by the superior electrode, while in FIG. 10(c) the middle electrode records ~55% of the energy recorded by the superior electrode. Similarly, in FIG. 10(b) the inferior electrode records ~25% of the original energy, while the inferior electrode in FIG. 10(c) records ~35% of the original energy. Comparing the two stimulation locations, FIG. 10(b) shows a 35% difference between middle and inferior electrodes, while FIG. 10(c) shows a 20% difference. This suggests a greater reflection, or a more constructive local energy interference, and thus a greater change in tendon tension and/or geometry, and thus a stronger muscle contraction in location 10(b).

After the suitable signal processing algorithms, such as those described above, have been used to select the optimally-located pair or group of stimulation electrodes in the array for energy delivery, a preferable embodiment of the method may commence a second optimization process to adjust the energy level and/or waveform shape that may be used to induce muscle contraction during the course of NMES therapy. This could involve applying different signal processing algorithms to data collected during the initial series of default stimulation events, or the collection of new electrical activity data during a second series of preset stimulation events using only the ideal pair or group of stimulation electrodes. Although numerous strategies for energy adjustment are possible, it is believed that as the stimulation energy is moved from an inefficient amplitude to a sufficiently strong amplitude, there may be a large increase in the amplitude of the response pulses contained in the electrical activity waveform measured by the sensing electrodes. In a preferable embodiment, the average electrical current carried by the train of stimulation pulses may be increased until the large change in response pulse amplitude is detected. Further, the waveform shape could be adjusted based upon feedback from the electrical activity waveform.

For example, if no large change in response pulse amplitude is detected, it could indicate that insufficient electrical energy may be reaching target muscles. In this scenario, it could be advantageous to employ the use of a sinusoidal (as opposed to biphasic square wave or other shaped) stimulation waveform, a waveform shape that has been shown to more effectively penetrate fatty tissue and other intermediate tissue layers that may lie between skin and muscle. As with previous stages of optimization, the NMES optimizations described in this paragraph may ideally be controlled by electronics, hardware, and/or firmware/software contained in the control unit. In alternate embodiments, portions or all of the controlling technology may be contained on the stimulation or sensing pads.

In another embodiment, sensing electrodes configured similarly to the setup shown in FIG. 10(a) may be used. Alternatively, additional configurations (such as those that use three or more electrodes in the tendon region) of sensing electrodes could be used without loss of generality. In this variation, each sensing electrode may record signals relative to a ground electrode (located, for example, over lower knee, shin, or other bony prominence) without the use of a differential amplifier. Accordingly, signals recorded during stimulation may generally be reflective of the stimulation pulses applied to the person, as circuitry may not be sufficiently sensitive to accurately record the response pulses that arise from electrical activity components produced by the muscle contraction. Benefits to this variation may include i) signal processing advantages associated with larger signal amplitude (stimulation pulses relative to EMG response—i.e., no need for amplification that may add noise, ii) improved performance in persons with low EMG strength or poor conduction of EMG signals to surface electrodes, and iii) consistent shape of recorded signals from the tendon region (ex. no need to detect whether recorded response pulses are monophasic, biphasic, etc.).

In this embodiment, the control unit may execute a default series of events that may include the stimulation of the target muscle with each potential pair or group of electrodes in an array. Additionally, multiple amplitudes of stimulation current, voltage, or energy may be used for each electrode pair or group. Electrical signals in slightly different regions of the mechanically connected tendon may be simultaneously recorded by sensing electrodes. These signals may be imported into signal processing algorithms, which may automatically choose the ideal anatomical location for stimulation and/or the stimulation parameters that are optimal for use.

For this embodiment, alternative signal processing techniques may be implemented to determine optimum electrode location, stimulation amplitude, and other parameters. Although differing from the algorithms associated with other variations of a preferable embodiment described above, these new algorithms may also use information related to tendon tension, geometry, and other properties to optimize stimulation parameters.

Algorithms used in conjunction with this variation of a preferable embodiment may analyze signals collected at individual sensing electrodes, may compare electrical signals collected at two or more sensing electrodes, or both. For example, some calculations may involve analyzing the average voltage amplitude at a single sensing electrode for different combinations of stimulation electrodes. Other calculations may compare waveform amplitudes, shapes, or other characteristics as stimulation signals may travel away from the stimulation zone and through the sensing region. These calculations may determine the difference, the ratio, or other relationships between voltage recordings made at multiple sensing electrodes.

A preferable approach to signal processing data collected in this embodiment may involve applying multiple levels of stimulation voltage, current, or energy to the person receiving NMES. For clear explanation, the following example uses the case of a constant-current stimulator device, although those skilled in the art will recognize that other type of stimulation devices (ex. constant-voltage, constant-power) could also be used without loss of generality. In one signal processing scheme, a sub-threshold current (ex. 10-20 mA) may first be applied to a person in the region of the target muscle once or more for every potential pair or group of stimulation electrodes, with the current level chosen to be sufficiently low that little to no muscle contraction is induced. Sensing electrode data may be recorded during each of these energy delivery periods. Following this, the current level may be increased to an amplitude (ex. 50-80 mA) capable of producing muscle contraction in most adults. The process may be repeated, and sensing electrode data may be recorded for each stimulation electrode pair or group. In one implementation, this may be done for two or more super-threshold current levels.

Following data collection described in the above paragraph, signal processing algorithms may be used to partially isolate electrical properties induced by muscle contraction from those that are constant or arising from other sources. This method may help account for factors, such as differing electrical impedance between potential pairs or groups of stimulation electrodes, that could bias results. This may be done by characterizing voltage data collected with reasonable assumptions and then mathematically manipulating the corresponding expressions using known parameters. For example, it can be reasonably assumed that the amplitude characteristics of voltage traces recorded by sensing electrodes during sub-threshold and super-threshold stimulation, respectively, can be described by:

$$V_s \propto I_s Z \qquad (1)$$

$$V_c \propto I_c Z + M \qquad (2),$$

where Vs and Vc are the peak voltage amplitudes resulting from each stimulation pulse during sub-threshold and super-threshold contraction, respectively, Is and Ic are the peak current amplitudes delivered by the stimulation electrodes during sub-threshold and super-threshold contraction, respectively, Z is the electrical impedance between the electrode pair or group used for stimulation, and M is a term describing the effect of tendon tension and/or geometry changes and/or other factors related to muscle contraction on the recorded signals. In Equation (2), the parameter M is modeled as an additive term; those skilled in the art will recognize that minor variations of Equation (2) and subsequent processing steps could incorporate the parameter M as a multiplicative term, exponential term, or several other mathematical representations.

Examination of Equation (1) indicates that, during sub-threshold stimulation, the peak amplitude of the voltage trace recorded at a sensing electrode is proportional to the sub-threshold current amplitude and the electrical impedance between the stimulation electrodes used. Equation (2) illustrates a similar case, but with super-threshold stimulation, where now a parameter (M) can be used to represent contributions to the recorded voltage trace that are associated with muscle contraction. Without wishing to be bound by any theory, it is believed that this parameter may be useful for determining the ideal pair or group of stimulation electrodes to be used during NMES and also optimal muscle stimulation parameters.

Using known characteristics of the muscle stimulation pulses and the sub-threshold recorded waveforms, it is possible to make mathematical adjustments to Vc so that the output of these adjustments is representative of the parameter M. Although many adjustment paradigms are possible, Equation (3) provides a representative example of one adjustment:

$$V_c^* = ([(V_c/V_s) - (I_c/I_s)] \times V_s) \quad (3).$$

Substitution of relationships that are evident in Equations (1) and (2) indicates that $V_c^* \approx M$. The process of obtaining $V_c^*$ from $V_c$ will be referred to as normalization.

A number of calculations or combinations of calculations may be used with normalized or non-normalized sensing electrode data to optimize stimulation electrode location and/or NMES parameters. For illustrative purposes, several of these calculations are described below, although those skilled in the art will recognize that other similar calculations are also suitable.

1) The relative voltage or energy amplitude recorded at a single sensing electrode (or, for a biphasic stimulation pulse, the relative maximum and/or minimum voltages). Without wishing to be bound by any theory, it is believed that larger amplitudes will represent more suitable stimulation locations.

2) The change in voltage or energy amplitude between sensing electrodes. It is believed that a larger change in energy recorded by electrodes located a fixed distance apart will represent more suitable stimulation locations. Here, 'change' could be analyzed with difference, ratio, or other operations.

3) If two or more super-threshold amplitudes are used, data from these sets of stimulation events (with or without normalization) may be compared. Comparisons are made with differences, ratios, or other means, and can be made using electrical data recorded by a single sensing electrode or using electrical data recorded at multiple electrodes. For example, if 60 and 80 mA currents were used to produce muscle contraction, a promising calculation is:

$$(V_{80}(1) - V_{80}(3)) - (V_{60}(1) - V_{60}(3)) \quad (4),$$

where $V(x)$ represents normalized or non-normalized voltage or energy for a given stimulation current value at the $x^{th}$ sensing electrode. Specifically, Equation (4) describes how the change in voltage or energy current between sensing electrodes 1 and 3 (for example, the superior and inferior electrodes in FIG. 10) differs for the 60 and 80 mA current levels of muscle stimulation. Without wishing to be bound by any theory, it is believed that larger values of Equation 4 and similar expressions will represent more suitable stimulation locations.

In another embodiment of the method, the control unit need not perform any sophisticated optimization of electrical stimulation parameters, such as waveform energy or shape. Instead, parameters may be pre-determined and set to default values. In this case, the only optimization step may involve the selection of the ideally-located pairs or groups of stimulation electrodes in the array to use during NMES therapy.

In an additional embodiment of the method and system, the control unit may not optimize what electrodes in the array are active to provide optimal NMES therapy. Instead, the control unit may cycle through a number of predetermined pairs or groups of electrodes, with each pair or group being active for a predetermined length of time. Each stimulation region (where the region is described by the location of the stimulation electrodes comprising the said pair or group) may have different characteristics, such as electrical impedance, that may require stimulation parameters to vary for each location in order to deliver equivalent therapy. Optimization algorithms in the control unit may adjust electrical stimulation parameters such that a safe and effective stimulation energy is provided for each stimulation location.

Following automated optimization and self-calibration, the control unit may automatically initiate energy delivery to the person receiving NMES. NMES may continue for a predetermined amount of time that is either specified by the operator or internally set by the control unit. Under normal modes of operation, energy delivery may terminate automatically following this predetermined period of time and provide an alert in the form of a sound, light, text message, other visual indicator, or other suitable mechanism to the operator. Alternatively, energy delivery can be terminated early under normal operating conditions by an operator or another person pressing an emergency shutoff button, knob, dial, switch, or other control on the control unit.

In yet another embodiment, the stimulation pads may contain only two stimulating electrodes, with one electrode serving as the 'reference' electrode. In this mode of operation, the operator may initiate therapy by pressing a button on either the stimulation pad or the control box or by performing another action. The control box may automatically optimize electrical stimulation parameters given feedback from the sensor element(s) in the pad, then initiate therapy automatically. In a variation of this embodiment, the control box may simply initiate NMES therapy automatically using a default set of parameters using no optimization.

Another embodiment of a NMES system could involve a stimulation pad without any sensor element(s). In this mode of operation, the operator would apply the stimulation pad to the target muscle and press a button on the control box or stimulation pad or perform another suitable action. The control box could automatically optimize features of the NMES therapy based upon information available from the stimulation electrodes. One example of this information is the electrical impedance sensed between active or non-active stimulation electrodes.

Safety Features and Burn Prevention

In a preferable embodiment of the method and system, automated safety features may be incorporated into a control unit and/or a stimulation pad. For example, temperature sensitive elements such as thermistors, thermocouples, infrared detectors, or other common electronic components known to those skilled in the art may be contained within or attached to the stimulation pad. The control unit may have one or more electrical channels to receive signals originating from these temperature sensitive elements. Upon receiving these signals, the control unit may have a means to process these data and evaluate whether the data indicate unsafe operating temperatures in the pad. This evaluation may be performed by an embedded microprocessor with associated software and/or firmware, an application specific integrated circuit, a field programmable gate array, a comparative means (ex. comparator with or without hysteresis), or other means that will be apparent to those skilled in the art.

If skin or electrode temperatures rise to 4° C. above baseline temperatures, the control unit may decrease the energy level delivered to the person by lowering the average electrical current carried by the train of stimulation pulses. In an alternate embodiment, the control unit may shift stimulation energy delivery temporarily or permanently to a different pair or group of stimulation electrodes in the array in response to this temperature rise. In a third embodiment, the mode of action may involve increasing the off-time (i.e., adjusting the duty cycle) between repeating series of stimulation events. If skin or electrode temperatures rise to 6° C. above baseline temperatures, the control unit may automatically terminate delivery of NMES therapy, and produce an alert that signals to the operator than unsafe operating conditions have been detected. Although 4° C. and 6° C. above baseline temperature are mentioned, any threshold temperature may be used to determine whether an action needs to be taken. Further discussion of safety features, such as burn prevention features, as discussed in greater detail below.

In one example of an NMES method with a safety feature, a health care provider untrained in NMES can begin by identifying a knee cap as a prominent anatomical marker and place a sensing pad appropriately as shown in FIG. 6. Once the sensing pad is placed, the notch/protrusion geometries of the stimulation and sensing pads may facilitate the proper placement of the stimulation pad roughly over the center of the quadriceps, the muscle group targeted for NMES. To accomplish sufficiently accurate placement, knowledge of muscle motor points is not required. Once the pads are placed, the operator may apply NMES therapy to the person by pressing a button located on either the control unit or stimulation pad. When pressed, this button may cause a system to automatically calibrate and subsequently begin delivering NMES. After a predetermined length of time, the control unit may automatically halt the delivery of NMES. The operator can return at their convenience to remove the stimulation and sensing pads from the person. In the event that an unsafe operating condition or other unexpected event is detected by the control unit, NMES therapy will automatically be terminated by the control unit, and an alert such as a periodic beeping noise and accompanying text message on an LCD screen will inform the operator of the problem.

The system may self-calibrate, which may ensure that the electrical stimulation parameters used during NMES are specified for maximum effectiveness while ensuring patient safety. Following calibration, NMES therapy may be delivered using automatically determined parameters, which may eliminate the need for a trained operator to manually select the parameters for use and markedly reducing the time required for an operator to implement therapy.

In another example of the method, a health care provider untrained in NMES can begin by identifying the target anatomy and place the stimulation pad roughly over the center of the muscle targeted. To do this, knowledge of muscle motor points is not required. Once the pad is placed, the operator may apply NMES therapy to the subject by pressing a button located on either the control box or stimulation pad. When pressed, this button may cause a system to automatically calibrate and subsequently begin delivering NMES. After a predetermined length of time, the control box may automatically halt the delivery of NMES. The operator can return at their convenience to remove the stimulation pad from the person.

There are several potential variations of the system embodiments described above, in addition to those variations already described in this disclosure. One variation utilizes an array of stimulating electrodes and sensing components contained in a soft, sleeve-like housing that is worn around a limb or strapped around a target region of interest. It should be apparent to those skilled in the art that the device and/or system described in both this paragraph and in the preceding paragraphs may be affixed to the person's skin in a variety of ways that may include the use of adhesives, sleeves, straps, ties, and Velcro strips. Modes of operation would be similar to those described above.

It is worth noting that a variation of the system disclosed herein may be useful as a stand-alone device independent of NMES therapy. Non-invasive assessment of tendon tension is seen as a worthwhile endeavor in the medical community and may have applications in the fields of orthopedics, nursing care, and others. For example, tendon tension has been suggested as a proxy for adequacy of repair or replacement of the anterior cruciate ligament. Variations of preferable embodiments of the system described herein may thus be utilized to measure tendon tension for a number of purposes other than the optimization of NMES.

Figure 11:
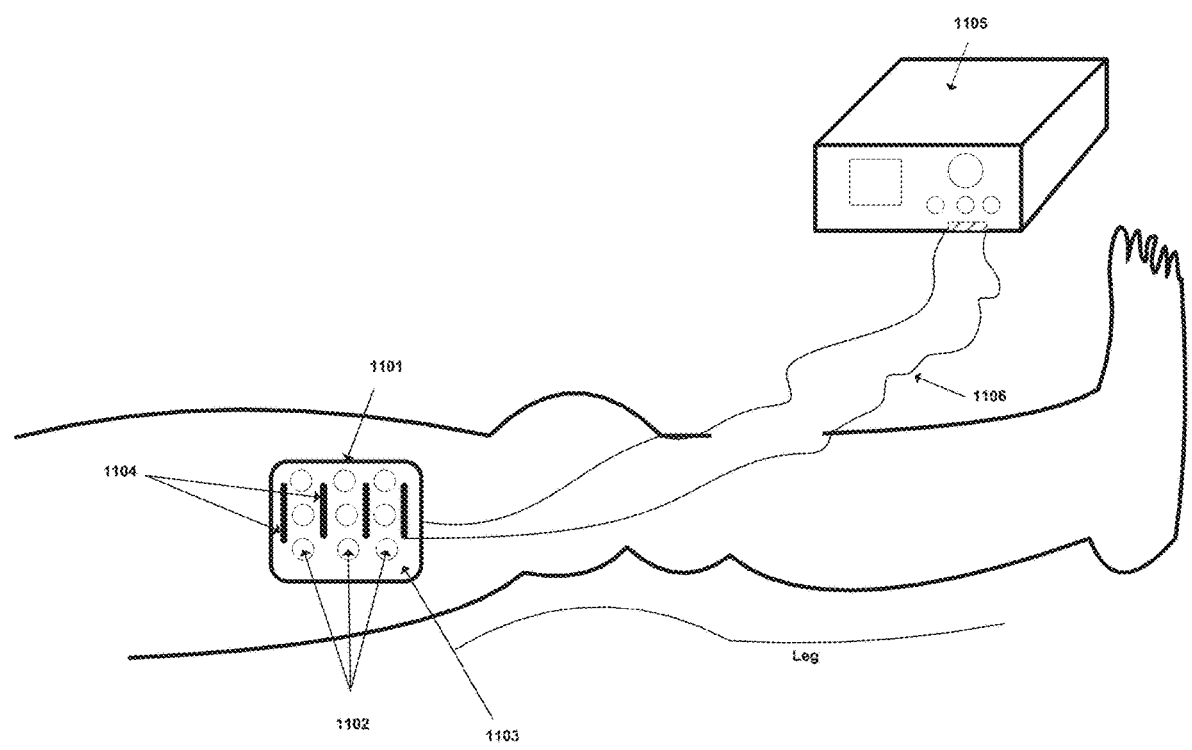
FIG. 11 provides an overview of an NMES device and system with the main components FIG. 12, several variations of a preferable embodiment of an NMES device and system.

FIG. 11 illustrates an embodiment of the device and system with a stimulation pad 1101 comprising an array of stimulating electrodes 1102 placed within a thin, flexible housing 1103. The stimulation pad may include temperature sensitive elements 1104, which may be located near the center of the stimulating electrode array. A control unit 1105 may comprise pulse generation electronics, a safety circuit designed to respond to temperature data from the pad, as well as both digital and analog signal processing components. In one embodiment, the control unit may communicate with the electrode array through a series of wire connections 1106.

The system may comprise two main functional components: a stimulation pad containing two or more stimulation electrodes and sensor element(s), and a control unit. The control unit may communicate with the stimulation pad through a wired connection, radiofrequency transmission, optical, acoustic, or electromagnetic signals, or another suitable mechanism. The control unit may be a separate unit that may be located some distance from the person receiving NMES therapy. In an alternate embodiment, the control unit may be integrated into a housing unit containing the stimulating electrode and sensing component(s).

In the described embodiment, the stimulation pad may comprise a thin and flexible housing with an adhesive backing that allows it to retain contact with the person receiving NMES. Alternatively, straps, hooks, Velcro, or other mechanisms may be used instead of or in addition to an adhesive backing to retain contact. Stimulation electrodes may be built into the pad in such a way that they make good electric contact with the skin and that they are electrically isolated from each other. Also contained within the housing may be one or more temperature sensitive elements and associated circuitry (if applicable) that can produce an electronic signal output that is reflective of absolute or relative local temperatures. These sensing elements may include thermistors, thermocouples, infrared detectors, or other common electronic components that will be apparent to those skilled in the art. In alternate embodiments, temperature sensitive elements may be provided in the proximity of the stimulation electrodes, but may or may not be in physical or thermal contact with the stimulation electrodes and/or the housing.

In another embodiment of the invention, the system may comprise a stimulation pad comprising two or more stimulation electrodes, a sensing pad comprising at least one sensor element, and a control unit. The stimulation pad may also comprise one or more temperature sensitive elements. Similarly, the sensing pad may also comprise one or more temperature sensitive element. In some embodiments, a separate pad or connection may be provided for temperature sensitive elements. The temperature sensitive elements may include thermistors, thermocouples, infrared detectors, or other common electronic components that will be apparent to those skilled in the art.

In some implementations, the temperature sensitive elements may have an oblong or elongated configuration. For example, the temperature sensitive element may have a lengthwise dimension that is greater than a widthwise dimension. The temperature sensitive elements may have any shape, including but not limited to ovals, rectangles, squares, circles, triangles, hexagons, or any other shape. In some instances, the temperature sensitive elements may have a different shape than a stimulating electrode, while in other embodiments, their shapes may be the same. In some instances, the temperature sensitive elements may be positioned such that they are oriented parallel to one another lengthwise. In other embodiments, some of the temperature sensitive elements may be parallel to one another while the other temperature sensitive elements may be perpendicular to one another. The temperature sensitive elements may have any orientation with respect to one another at any angle with respect to one another.

The temperature sensitive elements may be spaced apart from one another. In some embodiments, they may be positioned between stimulating electrodes. In some instances, the temperature sensitive elements may be positioned within an array of stimulating electrodes, or outside an array of stimulating electrodes, or both. The temperature sensitive elements may be positioned between stimulating electrodes and/or stimulating electrodes may be placed between the temperature sensitive elements. For example, an elongated temperature sensitive element may extend between rows of electrodes.

Figure 12:
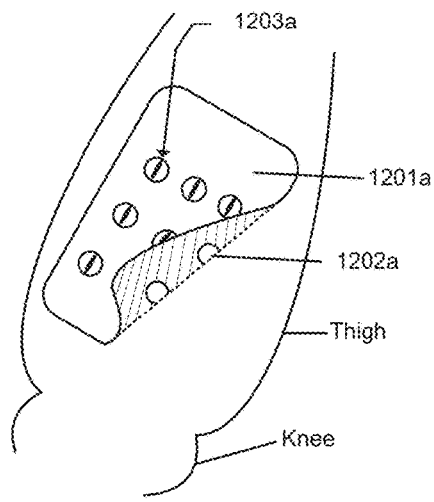
Figure 12:
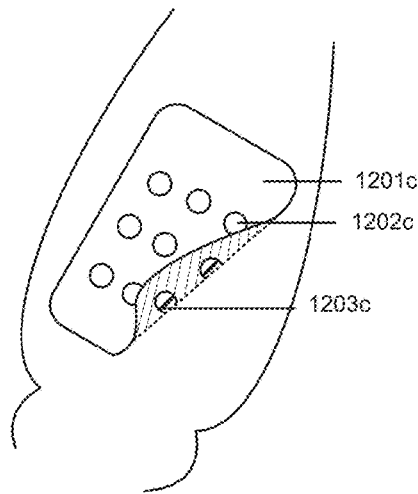
Figure 12:
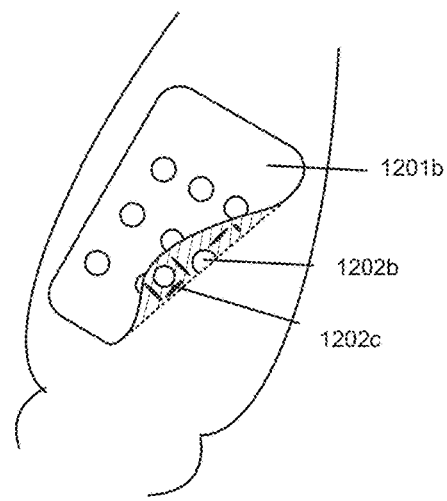
Figure 12:
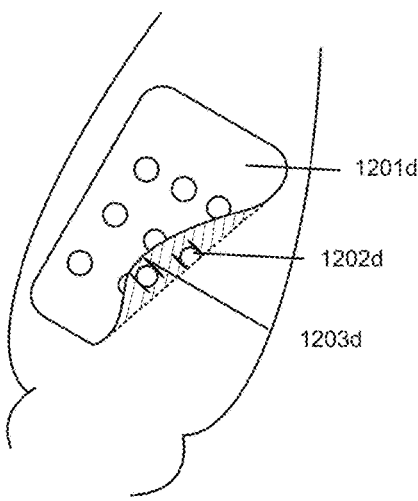

FIG. 12 provides four example embodiments of the device. The device may be placed over the quadriceps, over the front part of a thigh, above the knee. There are multiple potential variations of a preferable embodiment.

FIG. 12(a) illustrates an embodiment of the invention wherein temperature sensitive elements may embedded into or sit in very close proximity to a stimulation electrode. The device may include a thin, flexible housing 1201a, one or more electrode 1202a, and one or more temperature sensitive element 1203a. In this variation, temperature sensitive element may measure electrode or pad temperature, not the temperature of the skin directly. In some instances, the temperature sensitive element may be positioned on the electrode over the center of the electrode. For example, an elongated temperature sensitive element may substantially bisect an electrode.

FIG. 12(b) illustrates an embodiment of the invention where temperature sensitive elements may be located on the bottom side of a stimulation pad so that they are in contact or in the vicinity of a person's skin. The stimulation pad may include a thin, flexible housing 1201b, one or more electrode 1202b, and one or more temperature sensitive element 1203b. In some instances, the temperature sensitive element may measure the skin temperature, or the electrode and/or pad temperature. The temperature sensitive elements may be arranged so that they are not directly contacting the electrodes, but are disposed between the electrodes. The temperature sensitive elements may have any orientation between the electrodes. In some instances, when between electrodes, the shorter dimension (width) of the temperature sensitive element may be parallel to the direction between to the electrodes. Thus, the orientation of the temperature sensitive element (lengthwise) may extend perpendicular to an axis defined between the electrodes. However, any orientation or positioning of temperature sensitive elements may be provided.

FIG. 12(c) shows another embodiment of the invention, wherein the temperature sensitive elements may be located to detect temperatures at the skin-electrode interface. A stimulation pad may include a thin, flexible housing 1201c, one or more electrode 1202c, and one or more temperature sensitive element 1203c. The temperature sensitive element (s) may be built into bottom side of some or all of the electrodes so that temperatures are detected at the electrode/skin interface. In some instances, the temperature sensitive element may be positioned on the electrode over the center of the electrode. For example, an elongated temperature sensitive element may substantially bisect an electrode.

In FIG. 12(d), temperature sensitive elements may be located to detect temperature increases at the skin-electrode interface near the edges of the electrodes. A stimulation pad may include a thin, flexible housing 1201d, one or more electrode 1202d, and one or more temperature sensitive element 1203d. The temperature sensitive element(s) may be strategically placed at the skin/electrode interface near the edges of the electrode, where current density (and theoretically the risk of burns) is the highest. In some instances, the temperature sensitive elements may be parallel to one another. Alternatively, the temperature sensitive elements may be perpendicular to one another. The temperature sensitive elements may have any orientation along the edges of the electrode. It will be apparent to one skilled in the art that many other possible variations of these embodiments exist.

In a preferable embodiment, the control unit may contain components such as a signal generator, memory, processor, and power supply. When activated, the control unit may generate electrical stimulation signals that may be transmitted to the stimulation pad, which may couple the energy into the body to activate muscles. The electrical stimulation signal may be determined based on an input from a sensor, temperature sensitive element or both. In some variations of this embodiment, parameters that describe the electrical stimulation signals transmitted to the pad, such as the amplitude of stimulus, the shape of stimulus waveform, the duration of stimulus signal, and the stimulus signal frequency, may be adjusted by the user or by another mechanism (such as automatic adjustment/optimization). In this embodiment, the control unit may have one or more electrical channels to receive signals originating from the temperature sensitive elements in the stimulation pad. Upon receiving these signals, the control unit may have a means to process these data and evaluate whether the data indicate unsafe operating temperatures in the pad. This evaluation may be performed by an embedded microprocessor with associated software and/or firmware, an application specific integrated circuit, a field programmable gate array, a comparative means (ex. comparator with or without hysteresis), or other means that will be apparent to those skilled in the art. If unsafe operating conditions (i.e. a temperature higher than the maximum allowable temperature) are discovered upon evaluation, the control unit may take an action that immediately terminates or modifies delivery of NMES therapy.

Multiple variations are possible with regard to how the control unit terminates NMES therapy. In one variation, the control unit halts the output of energy, while informing a care provider through an audible alarm, flashing light/LED/LCD, or other alert mechanism that an unsafe operating condition has been detected. Another variation could involve halting energy output while disabling the stimulation pad and producing an alert signal to the care provider. The stimulation pad could be disabled by burning a fuse, destroying a control chip, or another similar means. In a third variation, the control unit could switch its energy output to a different electrode in an array of electrodes housed in the stimulation pad. In this scenario, if the cause of overheating was due to a malfunctioning electrode, NMES therapy could continue in a safe fashion with the use of a different electrode in the array. Following normal therapy termination, the control unit could disable the stimulation pad so that the faulty pad could not be utilized for an additional therapy session.

Figure 13:
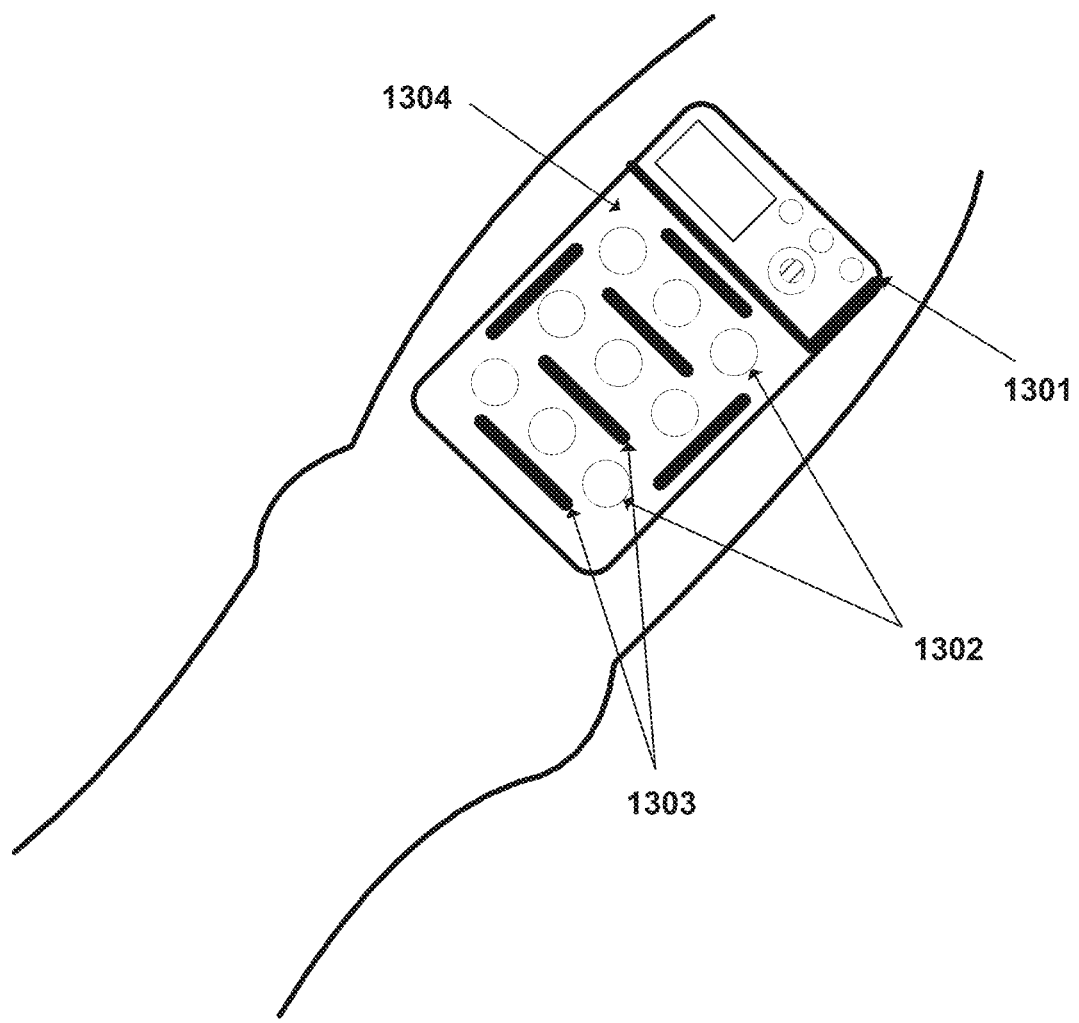
FIG. 13, an embodiment of an NMES device and system with a control unit integrated with an electrode array.

FIG. 13 shows an embodiment where the electrode array and the control unit may be integrated within a single unit. The single unit may include a control unit 1301, one or more electrodes 1302, and one or more temperature sensitive element 1303. In some embodiments, a thin, flexible housing may be provided 1304.

An NMES device and system could be comprised of a single, mechanically connected unit. In this case, the control unit 1301 may be built directly into the stimulation pad. Functional operation may be similar to the other embodiments described above. In this embodiment, it is conceivable that a temperature sensitive element could also be housed in the control unit itself.

Figure 14:
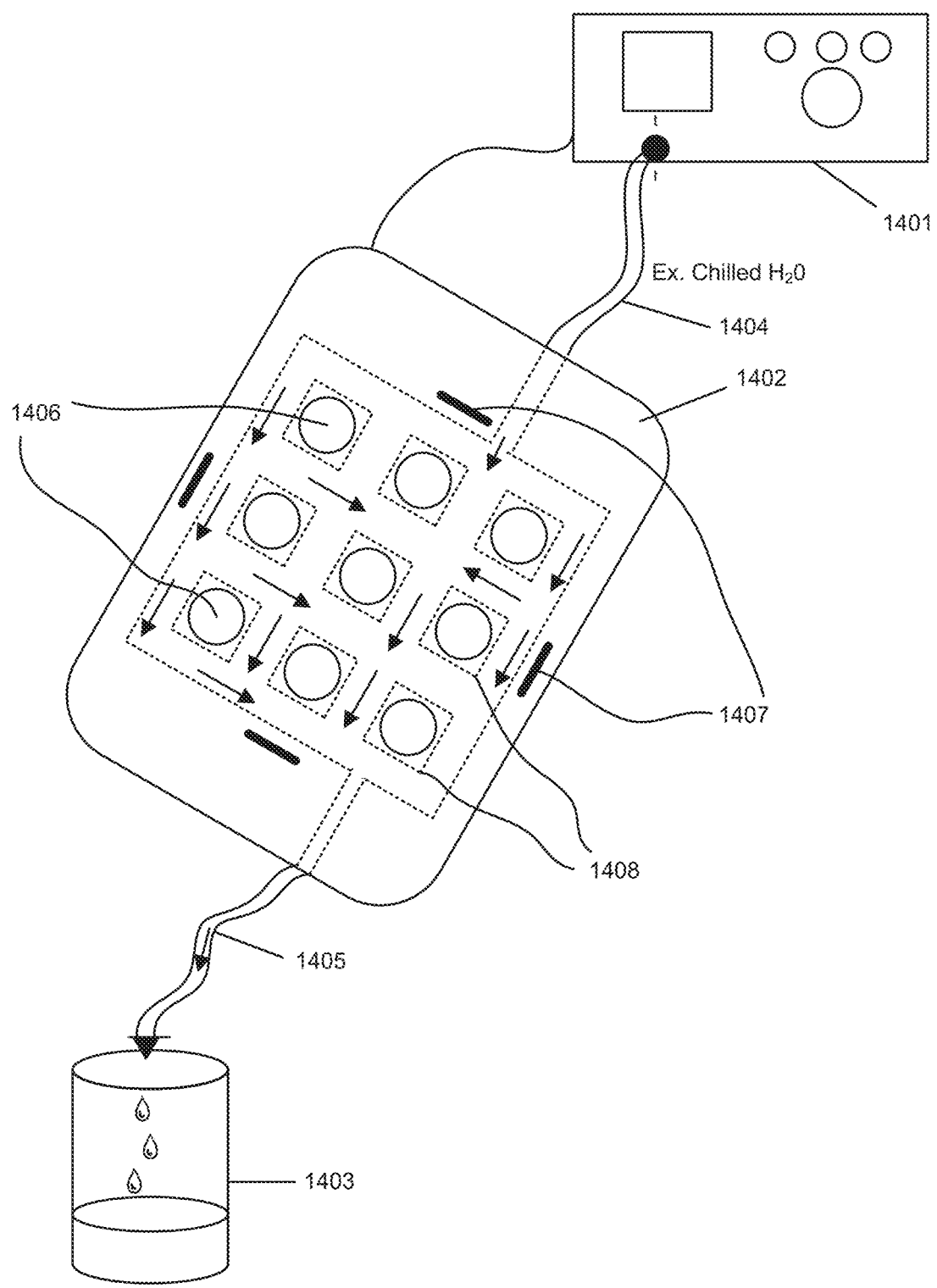
FIG. 14, an embodiment of an NMES device and system that utilizes an actively cooled stimulation pad.

FIG. 14 shows an embodiment of the invention that may utilize an actively cooled stimulation pad. In addition to the temperature sensor and software/firmware safeguards described above, this embodiment provides an additional layer of burn protection by maintaining stimulation pad temperature below body temperature. An active cooling assembly may be provided for the stimulation pad. An NMES device may include a control unit 1401, a stimulation pad 1402, and a fluid receiver 1403.

The control unit 1401 may be connected to a stimulation pad 1402 via a fluid transfer assembly 1404. In some embodiments, the fluid transfer assembly may be a tube or pipe, or any other structure that may enable fluid flow from the control unit to the stimulation pad. In some other embodiments, the fluid source need not be from the control unit, but may be from a separate fluid source (e.g., separate pump source) which may be connected to the stimulation pad via the fluid transfer assembly.

The stimulation pad 1402 may be connected to the fluid receiver 1403 via a second fluid transfer assembly 1405. In some embodiments, the second fluid transfer assembly may be a tube or pipe, or any other structure that may enable fluid flow from the stimulation pad to the fluid receiver. In some other embodiments, the fluid receiver may be different the fluid source. For example, if the fluid source is a control box, the fluid exiting the stimulation pad may flow to a fluid receiver that is not the control box. In another embodiment, the fluid receiver may be the same as the fluid source, or may somehow be coupled to the fluid source. For example, if the fluid source is a fluid reservoir, the fluid exiting may flow back into the fluid reservoir via the second fluid transfer assembly. In such situations, the fluid may cycle. In some instances, the fluid may cycle through a heat exchanger, or other mechanism that may reduce the temperature of the fluid exiting the stimulation pad.

The stimulation pad 1402 may comprise one or more electrode 1406, one or more temperature sensitive element 1407, and one or more irrigation channels 1408. The irrigation channels may be internal to the pad and may enable fluid flow through the pad. In some embodiments, the irrigation channels may surround the electrodes and/or temperature sensitive elements or flow between them.

Saline, chilled water, or other cool liquid, or cool air, or any other suitable gas or fluid may be pumped from the control unit or a separate pump source through channels embedded in the stimulation pad. Temperature sensitive elements located on the stimulation pad may continue to monitor temperature. The control unit will terminate NMES therapy if unsafe operating temperatures are detected.

Active cooling could also be accomplished through air circulation, materials, the use of a fan, heat sinks, and other methods apparent to those skilled in the art. In some embodiments, parameters related to active cooling may be variable. For example, the incoming fluid temperature and/or the fluid flow rate may be controllable. In some embodiments, which irrigation channels are accessed by the fluid may also be controllable. This embodiment reduces the likelihood of burns by cooling both electrodes and the skin surface during NMES therapy.

Figure 15:
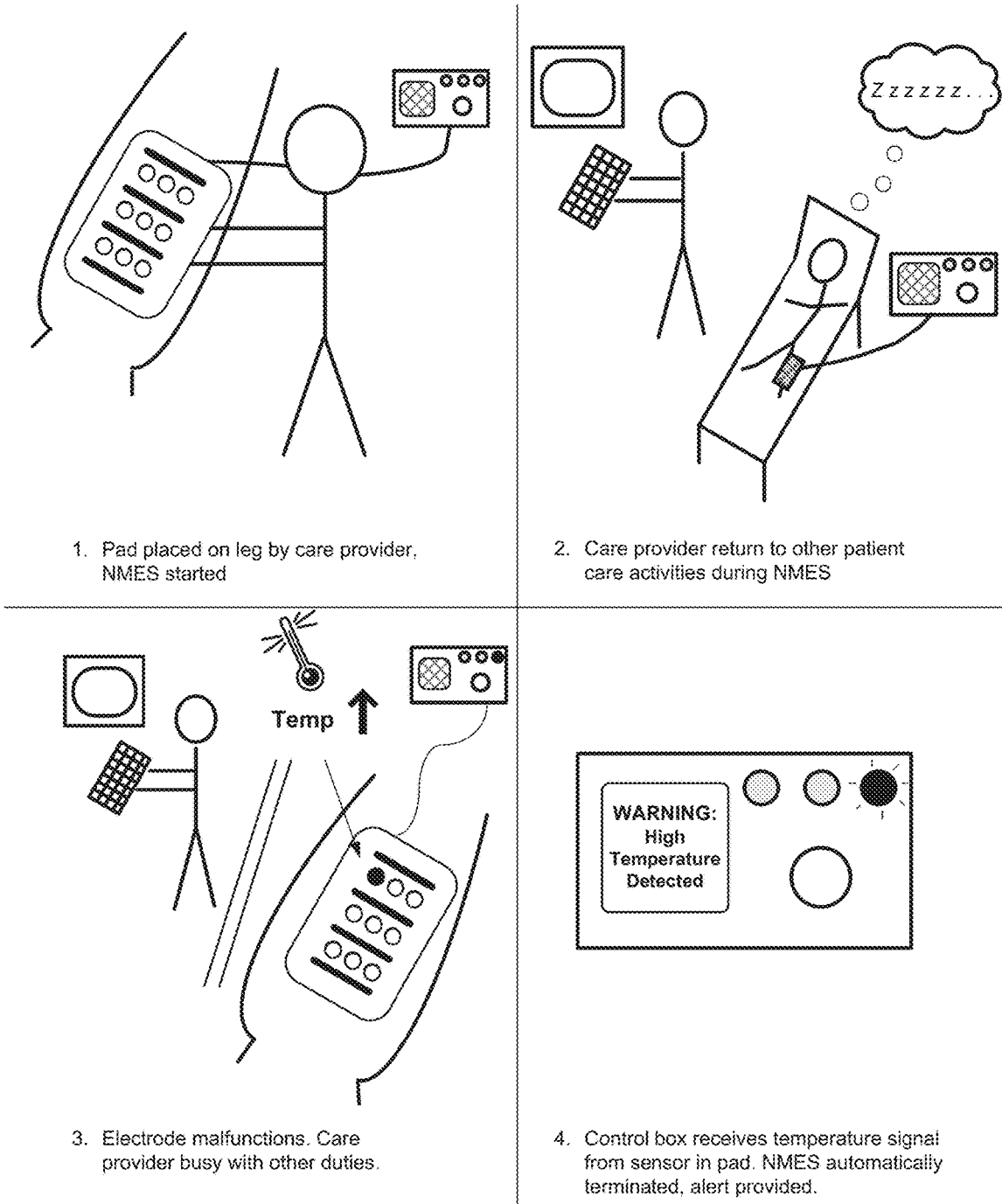
FIG. 15 provides an example of how an NMES device and system could be used.

FIG. 15 illustrates one possible scenario where an NMES device and system could prove very useful. (1) A medical care provider may place a stimulation pad with temperature sensors on the leg of a comatose or sedated patient. (2) The care provider may return to other patient care activities such as charting. (3) An electrode may malfunction or skin conditions may change, leading to an increase in local temperatures. The care provider may be otherwise occupied and does not notice promptly; the sedated/comatose patient has a reduced sensory threshold and does not react strongly to the local increase in temperature. (4) The control unit may receive information regarding the temperature increase from the sensors in the pad, and terminates NMES therapy automatically. Severe burns in the patient may be avoided.

In one embodiment of an NMES therapy method, an operator may place an electrode pad, which may contain stimulation electrodes and temperature sensitive element(s) on the body of a person receiving NMES treatment. The operator may initiate NMES, and may be alerted if temperature rises in the region of therapy approach unsafe levels. The operator may terminate NMES once the alert is provided. Alternatively, the operator may implement a system that may automatically disable NMES therapy if local temperatures are sensed to be approaching unsafe levels (posing a risk for burns).

In some embodiments, multiple temperature threshold levels may be provided that may cause different actions to be taken. For example, a first temperature threshold may be provided, that when exceeded, may cause the electrical stimulation parameters to be modified (e.g., providing lesser frequency stimulation, lesser amplitude of stimulation, or varying the electrodes that receive stimulation signals) or may cause parameters relating to a cooling assembly to be modified (e.g., decreasing source fluid temperature, or increasing fluid flow rate). A second temperature threshold may be provided, that when exceeded, may cause an alert to be sent to an operator. A third temperature threshold may be provided, that when exceeded, may cause termination of the NMES therapy. Any number of temperature thresholds at any desired temperatures may be provided, with corresponding actions when the temperature sensed by the temperature sensitive elements exceed the thresholds. In some embodiments, pre-existing protocols may be provided for such actions. Alternatively, such protocols may be operator-defined and programmed into a control unit.

In alternate embodiments of the invention, the cooling assembly may be utilized to vary and/or maintain the temperature in any manner. For example, in some instances, it may be desirable to warm an NMES device. In some embodiments, a target temperature or range of temperatures may be provided, and a temperature control assembly may control the device temperature to fall within the range. For example, cool fluid may be circulated when a temperature drop is desired, and warm fluid may be circulated when a temperature increase is desired.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A method of electrically stimulating a target muscle of a patient, comprising:
   placing at least one stimulation electrode in electrical contact with the target muscle;
   applying an electrical signal to the stimulation electrode;
   obtaining a signal from a sensing element placed on the patient, wherein the sensing element is configured to detect at least one biological parameter of the patient associated with contraction of the target muscle caused by the application of the electrical signal; and
   adapting stimulation of the target muscle by the at least one stimulation electrode using the obtained signal.

2. The method of claim 1, wherein the biological parameter is an electrophysiological signal generated by a second muscle of the patient or the target muscle.

3. The method of claim 1, wherein the biological parameter is a mechanical feature of the patient associated with contraction of the target muscle.

4. The method of claim 3, wherein the mechanical feature is at least one of a contraction distance, velocity, or acceleration.

5. The method of claim 1, wherein the biological parameter is a tendon signal obtained from a tendon that is associated with the target muscle contacted by the stimulation electrode.

6. The method of claim 5, wherein the tendon signal is at least one of a signal indicating tendon tension, a signal indicating tendon geometry, a signal indicating a change in tendon tension, or a signal indicating a change in tendon geometry.

7. The method of claim 1, wherein adapting comprises adapting at least one of a stimulation waveform, an energy level, or a stimulation frequency of an electrical single applied to the at least one stimulation electrode.

8. The method of claim 1, wherein the step of placing at least one stimulation electrode comprises placing a plurality of stimulation electrodes in electrical contact with the target muscle, and wherein adapting comprises selecting a subset of the plurality of the stimulation electrodes and stimulating the target muscle with only the subset of stimulation electrodes.

9. The method of claim 1, wherein adapting stimulation of the target muscle by the at least one stimulation electrode comprises adjusting at least one parameter of the electrical signal, and wherein the method further comprises applying a second electrical signal to the at least one stimulation electrode comprising the adjusted parameter.

10. A muscle stimulation system, comprising:
    at least one stimulation electrode adapted to be placed in electrical contact with a target muscle of a patient;
    a sensing element adapted to be placed on the patient, wherein the sensing element is configured to detect at least one biological parameter associated with contraction of the target muscle;
    an electrical stimulation energy source selectively communicable with the stimulation electrode and the sensing element; and
    a controller configured to adapt stimulation energy applied to the at least one stimulation electrode by the energy source in response to a biological parameter detected by the sensing element.

11. The system of claim 10, wherein the biological parameter is an electrophysiological signal generated by a second muscle of the patient or the target muscle.

12. The system of claim 10, wherein the biological parameter is a mechanical feature of the patient associated with contraction of the target muscle.

13. The system of claim 12, wherein the mechanical feature is at least one of a contraction distance, velocity, or acceleration.

14. The system of claim 10, wherein the biological parameter is a tendon signal obtained from a tendon that is associated with the target muscle contacted by the stimulation electrode.

15. The system of claim 14, wherein the tendon signal is at least one of a signal indicating tendon tension, a signal indicating tendon geometry, a signal indicating a change in tendon tension, or a signal indicating a change in tendon geometry.

16. The system of claim 10, wherein the controller is further configured to adapt stimulation energy applied to the at least one stimulation electrode by adapting at least one of a stimulation waveform, an energy level, or a stimulation frequency of an electrical single applied to the at least one stimulation electrode.

17. The system of claim 10, further comprising a plurality of stimulation electrodes adapted to be placed in electrical contact with the target muscle, and wherein the controller is further configured to adapt stimulation energy applied to the stimulation electrode by selecting a subset of the plurality of the stimulation electrodes and applying stimulation energy with only the subset of stimulation electrodes.

18. The system of claim 10, wherein the controller is further configured to:
    adapt stimulation energy applied to the at least one stimulation electrode by adjusting at least one parameter of the electrical signal; and
    apply a second electrical signal to the at least one stimulation electrode comprising the adjusted parameter.

19. The system of claim 10, wherein the at least one stimulation electrode is supported on an electrode substrate.

20. The system of claim 19, wherein the sensing element is supported on the electrode substrate.

* * * * *